(12) United States Patent
Miller et al.

(10) Patent No.: US 9,849,019 B2
(45) Date of Patent: Dec. 26, 2017

(54) METHODS AND SYSTEMS FOR OPTIMIZING DESIGN AND MANUFACTURE OF IMPLANT COMPONENTS USING SOLID FREEFORM FABRICATION

(71) Applicant: CONFORMIS, INC., Bedford, MA (US)

(72) Inventors: Bob Miller, Secaucus, NJ (US); David P. Hesketh, Methuen, MA (US); Ernest A. Dion, Danvers, MA (US)

(73) Assignee: ConforMIS, Inc., Billerica, MA (US)

( * ) Notice: Subject to any disclaimer, the term of this patent is extended or adjusted under 35 U.S.C. 154(b) by 543 days.

(21) Appl. No.: 14/033,350

(22) Filed: Sep. 20, 2013

(65) Prior Publication Data

US 2014/0086780 A1    Mar. 27, 2014

Related U.S. Application Data

(60) Provisional application No. 61/703,780, filed on Sep. 21, 2012, provisional application No. 61/704,712, filed on Sep. 24, 2012.

(51) Int. Cl.
*A61F 5/01*    (2006.01)
*A61F 2/30*    (2006.01)
*B33Y 80/00*    (2015.01)

(52) U.S. Cl.
CPC ............ *A61F 5/01* (2013.01); *A61F 2/30942* (2013.01); *A61F 2002/30962* (2013.01); *B33Y 80/00* (2014.12)

(58) Field of Classification Search
CPC .................... A61F 5/01; A61F 2/30942; A61F 2002/30962; B33Y 80/00
See application file for complete search history.

(56) References Cited

U.S. PATENT DOCUMENTS 4,673,409 A    6/1987    Van Kampen ................ 623/23
5,067,964 A    11/1991    Richmond et al. ............ 623/18
(Continued)

FOREIGN PATENT DOCUMENTS

CN    1480111 A    3/2004    ............ A61F 2/30
CN    101953726 A    1/2011    ............ A61F 2/28
(Continued)

OTHER PUBLICATIONS

Intergraph Corp. and Surgicad Corp., "Surgicad Design Combines 3-D Visualization with CAD Tools", Intergraph Corp. and Surgicad Corp. News Brief, 2 pages, Sep. 1993.
(Continued)

*Primary Examiner* — Charles Kasenge
(74) *Attorney, Agent, or Firm* — Sunstein Kann Murphy & Timbers LLP

(57) ABSTRACT

A method of manufacturing a plurality of orthopedic implant components is provided. The method includes providing a design for a first implant component having at least one dimension that is based on patient-specific information and a design for a second implant component having at least one dimension that is based on patient specific information. A build plan is created that includes a position and orientation for at least each of the first and second implant components within a build chamber of a solid freeform fabrication machine and with respect to a platform of the build chamber. The implants included in the build plan are produced by executing a build run of the solid freeform fabrication machine based on the build plan, wherein the plurality of implant components are positioned and oriented in an interleaved build configuration according to the build plan.

13 Claims, 15 Drawing Sheets

(56) References Cited

U.S. PATENT DOCUMENTS

| | | | |
|---|---|---|---|
| 5,246,530 A | 9/1993 | Bugle et al. | 156/643 |
| 5,365,996 A | 11/1994 | Crook | 164/45 |
| 5,507,820 A | 4/1996 | Pappas | 623/20 |
| 5,735,277 A | 4/1998 | Schuster | 128/653.1 |
| 6,206,927 B1 | 3/2001 | Fell et al. | 623/20.29 |
| 6,251,143 B1 | 6/2001 | Schwartz et al. | 623/23.72 |
| 6,254,639 B1 | 7/2001 | Peckitt | 623/11.11 |
| 6,280,478 B1 | 8/2001 | Richter et al. | 623/23.56 |
| 6,510,334 B1 | 1/2003 | Schuster et al. | 600/407 |
| 6,540,786 B2 | 4/2003 | Chibrac et al. | 623/18.11 |
| 6,632,246 B1 | 10/2003 | Simon et al. | 623/14.12 |
| 6,677,554 B2 | 1/2004 | Darrah et al. | |
| 6,679,917 B2 | 1/2004 | Ek | 623/20.14 |
| 6,694,207 B2 | 2/2004 | Darrah et al. | |
| 6,712,856 B1 | 3/2004 | Carignan et al. | 623/20.35 |
| 6,799,066 B2 | 9/2004 | Steines et al. | 600/407 |
| 6,905,514 B2 | 6/2005 | Carignan et al. | 623/20.35 |
| 6,932,842 B1 | 8/2005 | Litschko et al. | 623/16.11 |
| 6,978,188 B1 | 12/2005 | Christensen | 700/118 |
| 7,001,672 B2 | 2/2006 | Justin et al. | 428/615 |
| 7,172,596 B2 | 2/2007 | Coon et al. | 606/87 |
| 7,368,065 B2 | 5/2008 | Yang et al. | 216/83 |
| 7,445,640 B2 | 11/2008 | Despres, III et al. | 623/23.53 |
| 7,468,075 B2 | 12/2008 | Lang et al. | 623/16.11 |
| 7,603,192 B2 | 10/2009 | Martin et al. | 700/98 |
| 7,632,575 B2 | 12/2009 | Justin et al. | 428/615 |
| 7,718,109 B2 | 5/2010 | Robb et al. | 264/308 |
| 7,983,777 B2 | 7/2011 | Melton et al. | 700/98 |
| 8,021,154 B2 | 9/2011 | Holzner et al. | 433/223 |
| 8,070,752 B2 | 12/2011 | Metzger et al. | 606/88 |
| 8,086,336 B2 | 12/2011 | Christensen | 700/98 |
| 8,092,462 B2 | 1/2012 | Pinczewski et al. | 606/88 |
| 8,160,345 B2 | 4/2012 | Pavlovskaia et al. | 382/131 |
| 8,221,430 B2 | 7/2012 | Park et al. | 606/88 |
| 8,282,646 B2 | 10/2012 | Schoenefeld et al. | 606/88 |
| 8,311,306 B2 | 11/2012 | Pavlovskaia et al. | 382/131 |
| 8,337,508 B2 | 12/2012 | Lavallee et al. | 606/105 |
| 8,357,166 B2 | 1/2013 | Aram et al. | 606/88 |
| 8,377,066 B2 | 2/2013 | Katrana et al. | 606/86 |
| 8,377,068 B2 | 2/2013 | Aker et al. | 606/87 |
| 8,380,471 B2 | 2/2013 | Iannotti et al. | 703/6 |
| 8,398,646 B2 | 3/2013 | Metzger et al. | 606/88 |
| 8,407,067 B2 | 3/2013 | Uthgenannt et al. | 705/2 |
| 8,419,740 B2 | 4/2013 | Aram et al. | 606/88 |
| 8,425,524 B2 | 4/2013 | Aker et al. | 606/88 |
| 8,457,930 B2 | 6/2013 | Schroeder | 703/1 |
| 8,617,242 B2 | 12/2013 | Philipp | |
| 8,735,773 B2 | 5/2014 | Lang | |
| 8,801,720 B2 | 8/2014 | Park et al. | 606/88 |
| 8,888,480 B2* | 11/2014 | Yoo | B29C 67/0081 264/113 |
| 9,408,686 B1 | 8/2016 | Miller et al. | |
| 9,439,767 B2 | 9/2016 | Bojarski et al. | 606/86 R |
| 9,517,134 B2 | 12/2016 | Lang | |
| 9,579,110 B2 | 2/2017 | Bojarski et al. | |
| 9,636,229 B2 | 5/2017 | Lang et al. | |
| 2002/0028980 A1 | 3/2002 | Thierfelder et al. | 600/37 |
| 2002/0059049 A1 | 5/2002 | Bradbury et al. | 703/11 |
| 2002/0079601 A1 | 6/2002 | Russell et al. | 264/40.1 |
| 2002/0082741 A1 | 6/2002 | Mazumder et al. | 700/123 |
| 2003/0080957 A1 | 5/2003 | Stewart et al. | 345/420 |
| 2003/0236473 A1 | 12/2003 | Dore et al. | 600/587 |
| 2004/0098133 A1 | 5/2004 | Carignan et al. | 623/20.35 |
| 2004/0117015 A1 | 6/2004 | Biscup | 623/16.11 |
| 2005/0119664 A1 | 6/2005 | Carignan et al. | 606/96 |
| 2005/0137601 A1 | 6/2005 | Assell et al. | 606/79 |
| 2005/0148843 A1 | 7/2005 | Roose | 700/117 |
| 2005/0244239 A1 | 11/2005 | Shimp | 409/132 |
| 2005/0267584 A1 | 12/2005 | Burdulis, Jr. et al. | 623/20.19 |
| 2006/0069318 A1 | 3/2006 | Keaveny et al. | 600/300 |
| 2006/0136058 A1 | 6/2006 | Pietrzak | 623/13.14 |
| 2006/0241776 A1 | 10/2006 | Brown et al. | 623/20.16 |
| 2007/0005143 A1 | 1/2007 | Ek et al. | 623/20.32 |
| 2007/0118055 A1 | 5/2007 | McCombs | 600/587 |
| 2007/0118243 A1 | 5/2007 | Schroeder et al. | 700/118 |
| 2007/0142914 A1 | 6/2007 | Jones et al. | 623/14.13 |
| 2007/0198022 A1 | 8/2007 | Lang et al. | 606/88 |
| 2007/0226986 A1 | 10/2007 | Park et al. | 29/592 |
| 2007/0233141 A1 | 10/2007 | Park et al. | 606/88 |
| 2007/0288030 A1 | 12/2007 | Metzger et al. | 606/87 |
| 2008/0004709 A1 | 1/2008 | O'Neill et al. | 623/20.35 |
| 2008/0114370 A1 | 5/2008 | Schoenefeld | 606/96 |
| 2008/0147072 A1 | 6/2008 | Park et al. | 606/87 |
| 2008/0195216 A1 | 8/2008 | Philipp | 623/18.11 |
| 2008/0215059 A1 | 9/2008 | Carignan et al. | 606/96 |
| 2008/0257363 A1 | 10/2008 | Schoenefeld et al. | 128/897 |
| 2008/0262624 A1 | 10/2008 | White et al. | 623/20.32 |
| 2009/0088753 A1 | 4/2009 | Aram et al. | 606/79 |
| 2009/0099567 A1 | 4/2009 | Zajac | 606/79 |
| 2009/0110498 A1 | 4/2009 | Park | 408/1 |
| 2009/0131941 A1 | 5/2009 | Park et al. | 606/87 |
| 2009/0138020 A1 | 5/2009 | Park et al. | 606/88 |
| 2009/0151736 A1 | 6/2009 | Belcher et al. | 128/898 |
| 2009/0226068 A1 | 9/2009 | Fitz et al. | 382/131 |
| 2010/0049195 A1 | 2/2010 | Park et al. | 606/87 |
| 2010/0082035 A1 | 4/2010 | Keefer | 606/91 |
| 2010/0087829 A1 | 4/2010 | Metzger et al. | 606/96 |
| 2010/0152741 A1 | 6/2010 | Park et al. | 606/89 |
| 2010/0217270 A1* | 8/2010 | Polinski | A61F 2/0095 606/87 |
| 2010/0256479 A1 | 10/2010 | Park et al. | 600/410 |
| 2010/0332194 A1 | 12/2010 | McGuan et al. | 703/1 |
| 2011/0029091 A1 | 2/2011 | Bojarski et al. | 623/20.32 |
| 2011/0029093 A1* | 2/2011 | Bojarski | A61F 2/30942 623/20.35 |
| 2011/0071533 A1 | 3/2011 | Metzger et al. | 606/88 |
| 2011/0087332 A1* | 4/2011 | Bojarski | A61B 17/155 623/20.32 |
| 2011/0092804 A1 | 4/2011 | Schoenefeld et al. | 600/416 |
| 2011/0218545 A1 | 9/2011 | Catanzarite et al. | 606/96 |
| 2011/0264097 A1 | 10/2011 | Hodorek et al. | 606/88 |
| 2011/0266265 A1 | 11/2011 | Lang | 219/121.72 |
| 2012/0022659 A1 | 1/2012 | Wentorf | 623/20.32 |
| 2012/0078598 A1 | 3/2012 | Mcdaniel | 703/6 |
| 2012/0116203 A1 | 5/2012 | Vancraen et al. | 600/407 |
| 2012/0141034 A1 | 6/2012 | Iannotti et al. | 382/199 |
| 2012/0239045 A1 | 9/2012 | Li | 606/88 |
| 2012/0265496 A1 | 10/2012 | Mahfouz | 703/1 |
| 2012/0276509 A1 | 11/2012 | Iannotti et al. | 434/267 |
| 2012/0310364 A1 | 12/2012 | Li et al. | 623/23.55 |
| 2012/0316564 A1 | 12/2012 | Serbousek et al. | 606/80 |
| 2012/0323246 A1 | 12/2012 | Catanzarite et al. | 606/88 |
| 2013/0006250 A1 | 1/2013 | Metzger et al. | 606/87 |
| 2013/0035766 A1 | 2/2013 | Meridew | 623/22.21 |
| 2013/0066321 A1 | 3/2013 | Mannss et al. | 606/88 |
| 2013/0119579 A1 | 5/2013 | Iannotti et al. | 264/259 |
| 2013/0220570 A1* | 8/2013 | Sears | B22C 9/04 164/34 |
| 2013/0245803 A1 | 9/2013 | Lang | 700/98 |
| 2013/0253522 A1 | 9/2013 | Bojarski et al. | 606/88 |
| 2014/0039631 A1 | 2/2014 | Bojarski et al. | 623/18.11 |
| 2014/0065194 A1* | 3/2014 | Yoo | B29C 67/0081 424/400 |
| 2014/0086780 A1 | 3/2014 | Miller et al. | 419/1 |
| 2014/0109384 A1 | 4/2014 | Lang | 29/557 |
| 2014/0172111 A1 | 6/2014 | Lang et al. | 623/20.32 |
| 2014/0250677 A1 | 9/2014 | Lang | 29/592 |
| 2014/0259629 A1 | 9/2014 | Dion et al. | 29/558 |
| 2014/0324205 A1 | 10/2014 | Park et al. | 700/98 |
| 2015/0081029 A1 | 3/2015 | Bojarski et al. | 623/20.32 |
| 2015/0093283 A1 | 4/2015 | Miller et al. | 419/55 |
| 2017/0112626 A1 | 4/2017 | Miller et al. | |
| 2017/0119531 A1 | 5/2017 | Bojarski et al. | |
| 2017/0164957 A1 | 6/2017 | Bojarski et al. | |

FOREIGN PATENT DOCUMENTS

| | | | |
|---|---|---|---|
| CN | 102365061 A | 2/2012 | A61F 2/00 |
| DE | 3933459 | 4/1991 | A61F 2/00 |
| DE | 44 34 539 | 4/1996 | A61F 2/38 |
| DE | 10055465 | 5/2002 | A61L 24/00 |
| DE | 102006037067 | 2/2008 | C04B 41/87 |
| EP | 0 704 193 | 4/1996 | A61F 2/30 |

(56) References Cited

FOREIGN PATENT DOCUMENTS

| | | | | |
|---|---|---|---|---|
| EP | 1074229 | | 2/2001 | ............... A61F 2/38 |
| EP | 1683593 | | 7/2006 | .............. B22F 3/105 |
| EP | 2173260 | B1 | 4/2010 | ............. A61B 17/15 |
| JP | 7-236648 | A | 9/1995 | ............... A61F 2/28 |
| JP | 8-25487 | A | 1/1996 | ............. B29C 67/00 |
| JP | 9-169056 | A | 6/1997 | ............. B29C 67/00 |
| JP | 2004-166802 | A | 6/2004 | ............... A61F 2/38 |
| JP | 2005-532089 | A | 10/2005 | ............... A61F 2/38 |
| JP | 2007-236926 | A | 9/2007 | ............... A61F 2/36 |
| JP | 2010-538882 | A | 12/2010 | ............. B29C 67/00 |
| WO | WO 93/25157 | | 12/1993 | ............. A61B 17/56 |
| WO | WO 01/77988 | A2 | 10/2001 | ............. G06F 19/00 |
| WO | WO 03/094782 | A2 | 11/2003 | ............... A61F 2/00 |
| WO | WO 2004/047688 | | 6/2004 | ............... A61F 2/30 |
| WO | WO 2005/002473 | A1 | 1/2005 | ............... A61F 2/38 |
| WO | WO 2008/021494 | A2 | 2/2008 | ............. G06F 19/00 |
| WO | WO 2008/101090 | | 8/2008 | ............... A61F 2/38 |
| WO | WO 2009/001083 | | 12/2008 | ............. A61B 17/15 |
| WO | WO 2009/039159 | A2 | 3/2009 | ............. B29C 67/00 |
| WO | WO 2009/068892 | | 6/2009 | ............... A61C 9/00 |
| WO | WO 2009/106366 | | 9/2009 | ............. A61B 17/15 |
| WO | WO 2009/106816 | | 9/2009 | ............. A61B 19/00 |
| WO | WO 2010/099359 | A1 | 9/2010 | ............... A61F 2/00 |
| WO | WO 2010/148103 | | 12/2010 | ............. A61B 17/17 |
| WO | WO 2011/028624 | | 3/2011 | ............... A61F 2/38 |
| WO | WO 2011/056995 | | 5/2011 | ............... A61F 2/38 |
| WO | WO 2011/059641 | | 5/2011 | ............. A61B 17/15 |
| WO | WO 2011/094540 | A2 | 8/2011 | ............... A61F 2/38 |
| WO | WO 2011/101474 | A1 | 8/2011 | ............. G06F 19/00 |
| WO | WO 2011/109260 | A1 | 9/2011 | ............... A61F 2/30 |
| WO | WO 2011/130421 | | 10/2011 | ............. A61B 17/56 |
| WO | WO 2012/021241 | | 2/2012 | ............. A61B 17/88 |
| WO | WO 2012/021846 | | 2/2012 | ............. A61B 17/90 |
| WO | WO 2012/021894 | | 2/2012 | ............... A61F 2/46 |
| WO | WO 2012/021895 | | 2/2012 | ............... A61F 2/46 |
| WO | WO 2012/027150 | | 3/2012 | ............. G06F 19/00 |
| WO | WO 2012/051542 | | 4/2012 | ............. A61B 17/16 |
| WO | WO 2012/112698 | | 8/2012 | ............... A61F 2/30 |
| WO | WO 2013/152341 | A1 | 10/2013 | ............... A61F 2/38 |
| WO | WO 2013/155500 | | 10/2013 | ............... A61F 2/38 |
| WO | WO 2014/047514 | | 3/2014 | ............... A61F 2/56 |

OTHER PUBLICATIONS

Birnbaum et al., "Computer-Assisted Orthopedic Surgery With Individual Templates and Comparison to Conventional Operation Method", Spine, vol. 26, No. 4, pp. 365-369, Feb. 2001.
Brandt et al., In German: "CRIGOS—Development of a Compact Robot System for Image-Guided Orthopedic Surgery," *Der Orthopäde*, Springer-Verlag, vol. 29, No. 7, pp. 645-649 (Jul. 2000).
Brandt et al., English Translation with Certification: "CRIGOS—Development of a Compact Robot System for Image-Guided Orthopedic Surgery," *Der Orthopäde*, Springer-Verlag, vol. 29, No. 7, pp. 645-649 (Jul. 2000).
Chelule et al., "Patient-Specific Template to Preserve Bone Stock in Total Knee Replacement: Preliminary Results", *15th Annual ISTA Symposium*, Sep. 2002, 1 page.
Chelule et al., "Computer Aided Design of Personalized Jigs in Total Knee Replacement", 3rd Annual Meeting of CAOS Int'l Proc., Spain, Jun. 18, 21, 2003, pp. 58-59.
Froemel et al., "Computer Assisted Template Based Navigation for Total Knee Replacement", Documents presented at CAOS on Jun. 17, 2001, 4 pages.
Hafez et al., "Computer Assisted Total Knee Replacement: Could a Two-Piece Custom Template Replace the Complex Conventional Instrumentations?" Session 6: Novel Instruments; *Computer Aided Surgery*, Session 6, vol. 9, No. 3, pp. 93-94 (Jun. 2004).
Hafez et al., "Computer-assisted Total Knee Arthroplasty Using Patient-specific Templating," *Clinical Orthopaedics and Related Research*, No. 444, pp. 184-192 (Mar. 2006).
Hafez et al., "Computer Assisted Total Knee Replacement: Could a Two-Piece Custom Template Replace the Complex Conventional Instrumentations?", 4th Annual Meeting of CAOS Int'l Proc., Chicago, Jun. 16-19, 2004, pp. 63-64.
Hafez et al., "Computer-Assisted Total Hip Arthroplasty: The Present and the Future", Future Rheumatology., vol. 1, pp. 121-131, 2006.
Mumtaz et al., "Selective Laser Melting of Inconel 625 Using Pulse Shaping", Rapid Prototyping Journal, vol. 16, Iss. 4, pp. 248-257, 2010.
Petrovic et al., "Additive Manufacturing Solutions for Improved Medical Implants", Biomedicine, INTECH, pp. 148-180, Mar. 2012.
Portheine et al., "CT-Based Planning and Individual Template Navigation in TKA", Navigation and Robotics in Total Joint and Spine Surgery, Springer, 48:336-342 (2004).
Portheine et al., "Development of a Clinical Demonstrator for Computer Assisted Orthopedic Surgery with CT Image Based Individual Templates." In Lemke HU, Vannier MW, Inamura K (eds). Computer Assisted Radiology and Surgery. Amsterdam, Elsevier 944-949, 1997.
Portheine et al., "Computer-Assisted Total Knee Endoprosthetics with Planning-Specific Treatment Templates", Biomed. Tech., vol. 46, Supp. vol. 1, Jan. 2001—In German.
Portheine et al., "Computer-Assisted Total Knee Endoprosthetics with Planning-Specific Treatment Templates", Biomed. Tech., vol. 46, Supp. vol. 1, Jan. 2001—English translation.
Portheine et al., "Potentials of CT-based Planning and Template-based Procedure in Hip and Knee Surgery", Orth. Prac., vol. 36, pp. 786-791, 2000—In German.
Portheine et al., "Potentials of CT-based Planning and Template-based Procedure in Hip and Knee Surgery", Orth. Prac., vol. 36, pp. 786-791, 2000—English Translation.
Portheine et al., "Model-Based Operation Planning in Orthopedic Surgery", Thesis, RWTH Aachen University, Apr. 22, 2004, 90 pages—In German.
Portheine et al., "Model-Based Operation Planning in Orthopedic Surgery", Thesis, RWTH Aachen University, Apr. 22, 2004, 170 pages—English Translation.
Radermacher et al., "Computer Assisted Orthopedic Surgery by Means of Individual Templates •Aspects and Analysis of Potential Applications •" *Proceedings of the First International Symposium on Medical Robotics and Computer Assisted Surgery*, vol. 1: Sessions I-III, MRCAS '94, Pittsburgh, PA, pp. 42-48 (Sep. 22-24, 1994).
Radermacher, English Translation: Helmholtz Institute of Biomedical Technology, "Computer-Assisted Planning and Execution of Orthopedic Surgery Using Individual Surgical Templates", May 18, 1999.
Radermacher, German Version: Helmholtz Institute of Biomedical Technology, "Computer-Assisted Planning and Execution of Orthopedic Surgery Using Individual Surgical Templates", May 18, 1999.
Radermacher et al., "Computer Assisted Orthopaedic Surgery With Image Based Individual Templates" Clinical Orthopaedics, Sep. 1998, vol. 354, pp. 28-38.
Radermacher et al., "Image Guided Orthopedic Surgery Using Individual Templates—Experimental Results and Aspects of the Development of a Demonstrator for Pelvis Surgery." In Troccaz J. Grimson E., Mosges R (eds). Computer Vision, Virtual Reality and Robotics in Medicine and Medical Robotics and Computer Assisted Surgery, Lecture Notes in Computer Science. Berlin, Springer-Verlag 606-615, 1997.
Radermacher et al., "Computer Integrated Orthopedic Surgery—Connection of Planning and Execution in Surgical Inventions." In Taylor, R., Lavallee, S., Burdea G. Mosges, R. (eds). Computer Integrated Surgery. Cambridge, MIT press 451-463, 1996.
Radermacher et al., "Technique for Better Execution of CT Scan Planned Orthopedic Surgery on Bone Structures." In Lemke HW, Inamura, K., Jaffe, CC, Vannier, MW (eds). Computer Assisted Radiology, Berlin, Springer 933-938, 1995.
Radermacher et al., "CT Image Based Planning and Execution of Interventions in Orthopedic Surgery Using Individual Templates—Experimental Results and Aspects of Clinical Applications." In Nolte LP, Ganz, R. (eds). CAOS—Computer Assisted Orthopaedic Surgery. Bern, Hans Huber (in Press) 1998.

(56) References Cited

OTHER PUBLICATIONS

Radermacher, "Computer Assisted Matching of Planning and Execution in Orthopedic Surgery", Slide Presentation, San Diego, Nov. 29, 1993, 22 pages.
Radermacher, "Computer-Based Decision Support in the Selection and Evaluation of Contact Surfaces for Manual Referencing", Lecture presented at Helmholtz Meeting '98 and OSS '98, 1998, 6 pages—In German.
Radermacher, "Computer-Based Decision Support in the Selection and Evaluation of Contact Surfaces for Manual Referencing", Lecture presented at Helmholtz Meeting '98 and OSS '98, 1998, 8 pages—English Translation.
Radermacher, "Image Guided Orthopedic Surgery with Individual Templates", Helmhotz-Institute for Biomed. Eng., 2 pages, 1997.
Radermacher, "Template Based Navigation—An Efficient Technique for Hip and Knee Surgery", CAOS First Asian Meet, India, Mar. 27-28, 2004, pp. 44-50.
Radermacher, "Computer Assisted Matching of Planning and Execution in Orthopedic Surgery", IEEE, EMBS, San Diego, 1993, pp. 946-947.
Radermacher et al., "Computer Based Decision Support for the Planning of Contact Faces for Manual Registration with Individual Templates", Helmholtz-Institute for Biomed. Eng., 7 pages, 1997-98.
Radermacher et al., "Computer Integrated Advanced Orthopedics (CIAO)", 2nd European Conference on Eng. and Med., presented Apr. 26, 1993, 12 pages.
Radermacher et al., "Computer Integrated Surgery—Connecting Planning and Execution of Surgical Intervention in Orthopedics", Surgical Therapy Technology, Helmholtz-Institute Aachen Research Report, 1991-1992, pp. 187, 196-202.
Radermacher et al., "Computer-assisted operative interventions in orthopedics—are there prospects for endoprosthetics as well?", Prac. Ortho., vol. 27, pp. 149-164, 1997—In German.
Radermacher et al., "Computer-assisted operative interventions in orthopedics—are there prospects for endoprosthetics as well?", Prac. Ortho., vol. 27, pp. 1-17, 1997—English Translation.
Radermacher et al., "Computer-Assisted Planning and Operation in Orthopedics", Orth. Prac. 36th year, pp. 731-737, Dec. 2000—In German.
Radermacher et al., "Computer-Assisted Planning and Operation in Orthopedics", Orth. Prac. 36th year, pp. 731-737, Dec. 2000—English Translation.
Radermacher et al., "Surgical Therapy Technology", Helmholtz-Institut Aachen Research Report, 1993-1994, pp. 189-219.
Rau et al., "Small and Neat", Medical Tech. Int'l, pp. 65, 67 and 69, 1993-94.
Schiffers et al., In German: "Planning and execution of orthopedic surgery using individualized templates," Der Orthopäde, Springer-Verlag, vol. 29, No. 7, pp. 636-640, (Jul. 2000).
Schiffers et al., English Translation with Certification: "Planning and execution of orthopedic surgery using individualized templates," Der Orthopäde, Springer-Verlag, vol. 29, No. 7, pp. 636-640, (Jul. 2000).
Schkommodau et al., "Clinical Application of Individual Templates for Pedicle Screw Placement in Comparison to Computer Navigation", Poster presented at CAOS, Feb. 18, 2000, 1 page.
Schkommodau et al., "Clinical Experience With the Individual Template Technique", Orth. Prac., vol. 37, No. 1, pp. 19-22, 2001—In German.
Schkommodau et al., "Clinical Experience With the Individual Template Technique", Orth. Prac., vol. 37, No. 1, pp. 19-22, 2001—English Translation.
Seel et al., "Three-Dimensional Planning and Virtual Radiographs in Revision Total Hip Arthroplasty for Instability", Clinical Orthopaedics and Related Research, No. 442, pp. 35-38, Jan. 2006.
Staudte et al., "Computer-Assisted Operation Planning and Technique in Orthopedics", North Rhine-Westphalia Acad. for Sciences, Lecture N. 444, ISSN 0944-8799, 2000, 17 pages—In German.
Staudte et al., "Computer-Assisted Operation Planning and Technique in Orthopedics", North Rhine-Westphalia Acad. for Sciences, Lecture N. 444, ISSN 0944-8799, 2000, 34 pages—English Translation.
Thoma et al., In German: "Use of a New Subtraction Procedure Based on Three-Dimensional CT Scans for the Individual Treatment of Bone Defects in the Hip and Knee," Journal DGPW, No. 17, pp. 27-28 (May 1999).
Thoma et al., English Translation with Certification: "Use of a New Subtraction Procedure Based on Three-Dimensional CT Scans for the Individual Treatment of Bone Defects in the Hip and Knee," Journal DGPW, No. 17, pp. 27-28 (May 1999).
Thoma et al., In German: "Custom-made knee endoprosthetics using subtraction data of three-dimensional CT scans—A new approach," Der Orthopäde, Springer-Verlag, vol. 29, No. 7, pp. 641-644, (Jul. 2000).
Thoma et al., English Translation with Certification: "Custom-made knee endoprosthetics using subtraction data of three-dimensional CT scans—A new approach," Der Orthopäde, Springer-Verlag, vol. 29, No. 7, pp. 641-644, (Jul. 2000).
Wu et al., "Application of Laser Measuring, Numerical Simulation and Rapid Prototyping to Titanium Dental Castings", Dental Materials, vol. 17, pp. 102-108, 2001.
European Patent Office, Extended European Search Report—Application No. 12192903.8-1654 dated Apr. 17, 2013, 8 pages.
European Patent Office, Extended European Search Report—Application No. 13775348.9-1654 dated Mar. 10, 2015, 6 pages.
International Searching Authority, International Search Report—International Application No. PCT/US2012/025274, dated Oct. 25, 2012, together with the Written Opinion of the International Searching Authority, 12 pages.
International Searching Authority, International Search Report—International Application No. PCT/US2013/061042 dated Jan. 10, 2014, together with the Written Opinion of the International Searching Authority, 12 pages.
International Searching Authority, International Search Report—International Application No. PCT/US2008/05377, dated Sep. 30, 2008, together with the Written Opinion of the International Searching Authority, 17 pages.
International Searching Authority, International Search Report—International Application No. PCT/US2013/036505 dated Jul. 29, 2013, together with the Written Opinion of the International Searching Authority, 7 pages.
International Searching Authority, Invitation to Pay Additional Fees—International Application No. PCT/US2008/053977, dated Jul. 11, 2008, together with the Written Opinion of the International Searching Authority, 6 pages.
Chinese Patent Office, Search Report dated Mar. 3, 2016, 2 pages.
Japanese Patent Office, In Japanese: Office Action pertaining to Japanese Patent Application No. 2015-505970 dated Nov. 24, 2015, 2 pages.
Japanese Patent Office, English Translation: Office Action pertaining to Japanese Patent Application No. 2015-505970 dated Nov. 24, 2015, 4 pages.
European Patent Office, Partial Supplementary European Search Report Application No. 13771863.1-1654, dated Apr. 26, 2016, 7 pages.
International Searching Authority, International Search Report—International Application No. PCT/US2013/035536 dated Jul. 18, 2013, together with the Written Opinion of the International Searching Authority, 9 pages.
U.S. Appl. No. 12/031,239, filed Feb. 14, 2008.
U.S. Appl. No. 12/712,827, filed Feb. 25, 2010.
U.S. Appl. No. 13/157,857, filed Jun. 10, 2011.
U.S. Appl. No. 13/746,742, filed Jan. 22, 2013.
U.S. Appl. No. 13/887,712, filed May 6, 2013.
U.S. Appl. No. 13/892,547, filed May 13, 2013.
U.S. Appl. No. 14/033,095, filed Sep. 20, 2013.
U.S. Appl. No. 14/051,003, filed Oct. 10, 2013.
U.S. Appl. No. 14/134,064, filed Dec. 19, 2013.
U.S. Appl. No. 14/216,473, filed Mar. 17, 2014.
U.S. Appl. No. 14/285,151, filed May 22, 2014.
U.S. Appl. No. 14/389,987, filed Apr. 6, 2013.
U.S. Appl. No. 14/390,829, filed Apr. 13, 2013.

\* cited by examiner

METHODS AND SYSTEMS FOR OPTIMIZING DESIGN AND MANUFACTURE OF IMPLANT COMPONENTS USING SOLID FREEFORM FABRICATION

RELATED APPLICATIONS

This application claims the benefit of U.S. Provisional Application No. 61/703,780, entitled "Methods and Systems for Optimizing Design and Manufacture of Implant Components Using Solid Freeform Fabrication" and filed Sep. 21, 2012, the disclosure of which is incorporated herein by reference in its entirety. This application also claims the benefit of U.S. Provisional Application No. 61/704,712, entitled "Methods and Systems for Optimizing Design and Manufacture of Implant Components Using Solid Freeform Fabrication" and filed Sep. 24, 2012, the disclosure of which is incorporated herein by reference in its entirety.

TECHNICAL FIELD

This application relates to methods and systems for manufacturing implants, implant components, and/or related tools using solid freeform fabrication technologies.

BACKGROUND

Recently, the joint replacement field has come to embrace the concept of "patient-specific" and "patient-engineered" implant systems. With such systems, the implants, associated tools, and procedures are designed or otherwise modified to account for and accommodate the individual anatomy of the patient undergoing the surgical procedure. Such systems typically utilize non-invasive imaging data, taken of the patient pre-operatively, to guide the design and/or selection of the implant, surgical tools, and the planning of the surgical procedure itself. Various objectives of these newer systems can include: (1) reducing the amount of bony anatomy removed to accommodate the implant, (2) designing/selecting an implant that replicates and/or improves the function of the natural joint, (3) increasing the durability and functional lifetime of the implant, (4) simplifying the surgical procedure for the surgeon, (5) reducing patient recovery time and/or discomfort, and/or (6) improving patient outcomes.

Because "patient-specific" and "patient-engineered" implant systems are created using anatomical information from a particular patient, such systems are generally created after the patient has been designated a "surgical candidate" and undergone non-invasive imaging. But, because such systems are not generally pre-manufactured and stockpiled in multiple sizes (as are traditional systems), there can be a considerable delay between patient diagnosis and the actual surgery, much of which is due to the amount of time necessary to design and manufacture the "patient-specific" and/or "patient-engineered" implant components using patent image data.

A significant portion of any delay between patient diagnosis/imaging and actual surgery can often be attributed to the time needed to manufacture each "patient-specific" and/or "patient-engineered" implant system to a particular patient's anatomy. Usually, such implants are manufactured individually or in small batches, using a 3rd party vendor, which can greatly increase the cost of creating such implant components (as measured on a per-implant basis) when compared to the large batch manufacturing used with traditional non-custom implants.

Accordingly, there is a need in the art for advanced methods, techniques, devices and systems to ensure the availability of "patient-specific" and/or "patient-engineered" implant components for a scheduled surgery in a cost effective and efficient manner.

DETAILED DESCRIPTION

Figure 1:
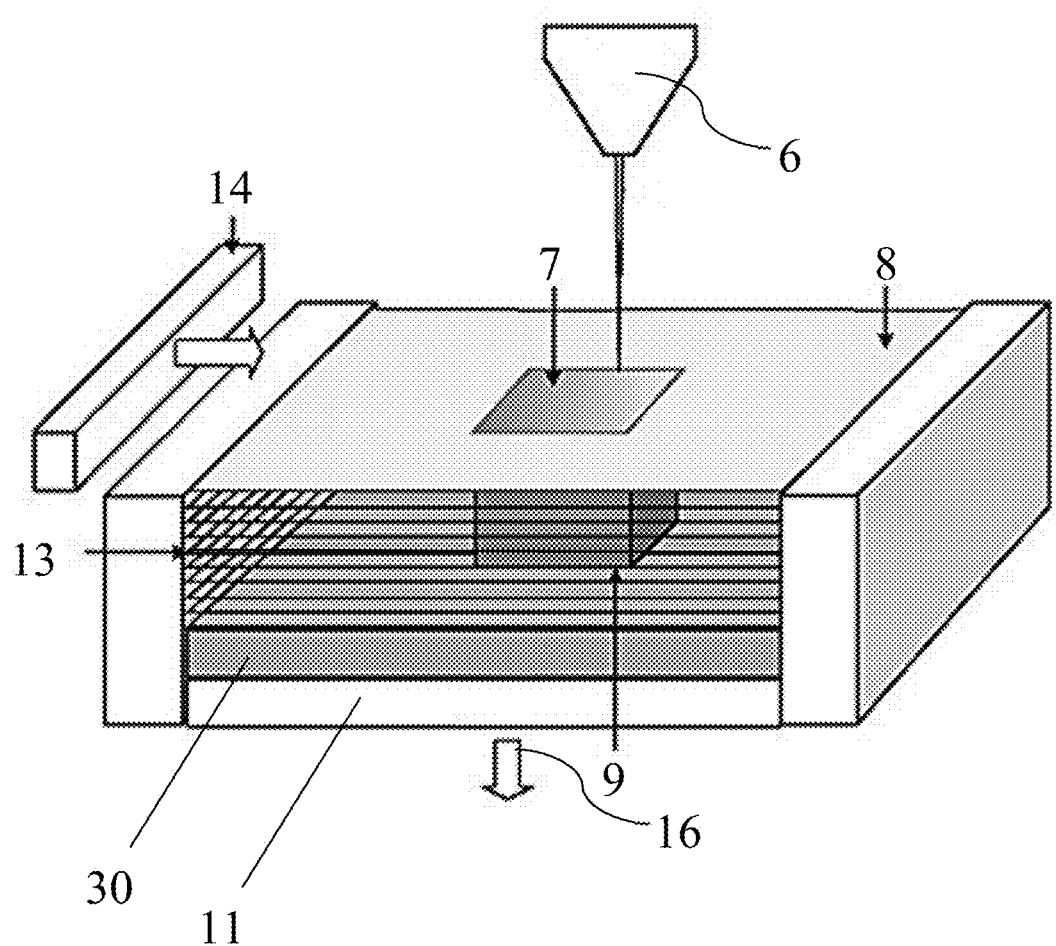
FIG. 1 depicts a schematic view of equipment and the process used in a typical SLM/DMLS manufacturing process.

A number of significant challenges face the widespread adoption of patient-specific implants and associated surgical procedures, many of which relate to the amount of time required to manufacture the implant, as well as the significant costs associated with creating a unique implant and/or implant component for each individual surgical patient. Unlike standard and/or modular implants, which can be manufactured in bulk and stored for use as needed, patient-specific implants are generally created after a patient has been identified as a surgical candidate, and the implant is designed and/or selected using imaging data taken of the intended patient's anatomy. The process of designing, manufacturing and finishing the implant can involve a number of steps, typically involving multiple vendors and capital-intensive heavy equipment such as casting equipment and/or forges, and this process must result in an acceptable implant before the surgery can occur. In some cases, traditional methods of creating of a patient-specific implant from patient imaging data can require more than 4 to 7 weeks, which is a significant and often unacceptable delay for both the surgeon and the patient.

An additional challenge facing the acceptance of patient-specific implants relates to the significant costs associated with creating a unique implant for each individual patient. The unique nature of each patient-specific implant does not lend their creation to bulk manufacturing methods including high-volume casting techniques. Rather, individual implant components are generally designed and investment cast on an individual basis, or can be designed and machined from bulk raw materials, both of which can be a time-consuming and expensive process. In most cases, the expense of creating unique molds and/or tooling necessary to create the patient-specific implant is assigned to the single unique implant (or to a small quantity of such implants), as there is no large volume of manufactured parts among which the expense can be shared or distributed.

Various technologies appropriate for manufacturing implants and tools are known in the art, for example, as described in Wohlers Report 2009, *State of the Industry Annual Worldwide Progress Report on Additive Manufacturing*, Wohlers Associates, 2009 (ISBN 0-9754429-5-3), available from the web www.wohlersassociates.com; Pham and Dimov, *Rapid manufacturing*, Springer-Verlag, 2001 (ISBN 1-85233-360-X); Grenda, *Printing the Future, The 3D Printing and Rapid Prototyping Source Book*, Castle Island Co., 2009; *Virtual Prototyping & Bio Manufacturing in Medical Applications*, Bidanda and Bartolo (Eds.), Springer, Dec. 17, 2007 (ISBN: 10: 0387334297; 13: 978-0387334295); *Bio-Materials and Prototyping Applications in Medicine*, Bártolo and Bidanda (Eds.), Springer, Dec. 10, 2007 (ISBN: 10: 0387476822; 13: 978-0387476827); Liou, *Rapid Prototyping and Engineering Applications: A Toolbox for Prototype Development*, CRC, Sep. 26, 2007 (ISBN: 10: 0849334098; 13: 978-0849334092); *Advanced Manufacturing Technology for Medical Applications: Reverse Engineering, Software Conversion and Rapid Prototyping*, Gibson (Ed.), Wiley, January 2006 (ISBN: 10: 0470016884; 13: 978-0470016886); and Branner et al., "Coupled Field Simulation in Additive Layer Manufacturing," 3rd International Conference PMI, 2008 (10 pages).

TABLE

Exemplary techniques for forming or altering a patient-specific and/or patient-engineered implant component for a patient's anatomy

| Technique | Brief description of technique and related notes |
| --- | --- |
| CNC | CNC refers to computer numerically controlled (CNC) machine tools, a computer-driven technique, e.g., computer-code instructions, in which machine tools are driven by one or more computers. Embodiments of this method can interface with CAD software to streamline the automated design and manufacturing process. |
| CAM | CAM refers to computer-aided manufacturing (CAM) and can be used to describe the use of software programming tools to efficiently manage manufacturing and production of products and prototypes. CAM can be used with CAD to generate CNC code for manufacturing three-dimensional objects. |
| Casting, including casting using rapid prototyped casting patterns | Casting is a manufacturing technique that employs a mold. Typically, a mold includes the negative of the desired shape of a product. A liquid material is poured into the mold and allowed to cure, for example, with time, cooling, and/or with the addition of a solidifying agent. The resulting solid material or casting can be worked subsequently, for example, by sanding or bonding to another casting to generate a final product. |
| Welding | Welding is a manufacturing technique in which two components are fused together at one or more locations. In certain embodiments, the component joining surfaces include metal or thermoplastic and heat is administered as part of the fusion technique. |
| Forging | Forging is a manufacturing technique in which a product or component, typically a metal, is shaped, typically by heating and applying force. |
| Rapid prototyping | Rapid prototyping refers generally to automated construction of a prototype or product, typically using an additive manufacturing technology, such as EBM, SLS, SLM, SLA, DMLS, 3DP, FDM and other technologies |
| EBM ® | EBM ® refers to electron beam melting (EBM ®), which is a powder-based additive manufacturing technology. Typically, successive layers of metal powder are deposited and melted with an electron beam in a vacuum. |
| SLS | SLS refers to selective laser sintering (SLS), which is a powder-based additive manufacturing technology. Typically, successive layers of a powder (e.g., polymer, metal, sand, or other material) are deposited and melted with a scanning laser, for example, a carbon dioxide laser. |
| SLM | SLM refers to selective laser melting ™ (SLM), which is a technology similar to SLS; however, with SLM the powder material is fully melted to form a fully-dense product. |
| SLA or SL | SLA or SL refers to stereolithography (SLA or SL), which is a liquid-based additive manufacturing technology. Typically, successive layers of a liquid resin are exposed to a curing, for example, with UV laser light, to solidify each layer and bond it to the layer below. This technology typically requires the additional and removal of support structures when creating particular geometries. |

TABLE-continued

Exemplary techniques for forming or altering a patient-specific and/or
patient-engineered implant component for a patient's anatomy

| Technique | Brief description of technique and related notes |
|---|---|
| DMLS | DMLS refers to direct metal laser sintering (DMLS), which is a powder-based additive manufacturing technology. Typically, metal powder is deposited and melted locally using a fiber optic laser. Complex and highly accurate geometries can be produced with this technology. This technology supports net-shaping, which means that the product generated from the technology requires little or no subsequent surface finishing. |
| LC | LC refers to LaserCusing ®(LC), which is a powder-based additive manufacturing technology. LC is similar to DMLS; however, with LC a high-energy laser is used to completely melt the powder, thereby creating a fully-dense product. |
| 3DP | 3DP refers to three-dimensional printing (3DP), which is a high-speed additive manufacturing technology that can deposit various types of materials in powder, liquid, or granular form in a printer-like fashion. Deposited layers can be cured layer by layer or, alternatively, for granular deposition, an intervening adhesive step can be used to secure layered granules together in bed of granules and the multiple layers subsequently can be cured together, for example, with laser or light curing. |
| LENS | LENS ® refers to Laser Engineered Net Shaping ™ (LENS ®), which is a powder-based additive manufacturing technology. Typically, a metal powder is supplied to the focus of the laser beam at a deposition head. The laser beam melts the powder as it is applied, in raster fashion. The process continues layer by and layer and requires no subsequent curing. This technology supports net-shaping, which means that the product generated from the technology requires little or no subsequent surface finishing. |
| FDM | FDM refers to fused deposition modeling ™ (FDM) is an extrusion-based additive manufacturing technology. Typically, beads of heated extruded polymers are deposited row by row and layer by layer. The beads harden as the extruded polymer cools. |

Solid Freeform Fabrication (SFF) includes a group of emerging technologies that have revolutionized product development and manufacturing. The common feature shared by these technologies is the ability to produce freeform, complex geometry components directly from a computer generated model. SFF processes generally rely on the concept of layerwise material addition in selected regions. A computer generated model serves as the basis for making a replica. The model is mathematically sliced and each slice is recreated in the material of choice to build a complete object. A typical SFF machine can be likened to a miniaturized "manufacturing plant" representing the convergence of mechanical, chemical, electrical, materials and computer engineering sciences.

Patient-specific and/or patient-engineered implants can be produced using 3-dimensional printing technology (also known as Solid Freeform Fabrication or "SFF") to create solid, physical implant components from an electronic or computerized data file (e.g., a CAD file). 3D printing techniques such as Selective Laser Sintering (SLS), EBM (Electron Beam Melting) and Selective Laser Melting (SLM—also known as Direct Metal Laser Sintering—DMLS—or LaserCusing) can allow the creation of durable metallic objects that are biocompatible and can directly serve as implant components.

In certain embodiments, an implant can include components and/or implant component parts produced via various methods. For example, in certain embodiments for a knee implant, the knee implant can include a metal femoral implant component produced by casting or by an additive manufacturing technique and having a patient-specific femoral intercondylar distance; a tibial component cut from a blank and machined to be patient-specific for the perimeter of the patient's cut tibia; and a tibial insert having a standard lock and a top surface that is patient-specific for at least the patient's intercondylar distance between the tibial insert dishes to accommodate the patient-specific femoral intercondylar distance of the femoral implant.

As another example, in certain embodiments a knee implant can include a metal femoral implant component produced by casting or by an additive manufacturing technique that is patient-specific with respect to a particular patient's M-L dimension and standard with respect to the patient's femoral intercondylar distance; a tibial component cut from a blank and machined to be patient-specific for the perimeter of the patient's cut tibia; and a tibial insert having a standard lock and a top surface that includes a standard intercondylar distance between the tibial insert dishes to accommodate the standard femoral intercondylar distance of the femoral implant.

As with any manufacturing process, including traditional processes such as the casting, forging and/or machining of metals, the various advantages of different metal and/or plastic 3D printing techniques typically are accompanied by various disadvantages and/or limitations, which may vary depending upon the type of printing technique chosen. In many cases, implant components created through various metal and plastic 3D printing techniques can (1) be limited in the range of potential implant materials, (2) often have a rough grainy and porous surface finish, (3) often experience high temperature gradients that can result in a build-up of thermal stresses, (4) typically experience a relatively large shrink rate that can cause the part (or portions thereof) to warp, bow or curl, (5) undergo a rapid solidification, often leading to the occurrence of segregation phenomena and the presence of non-equilibrium phases, (6) have a surface feature detail that is relatively coarse, and the object can have a surface roughness created by the layer-wise building techniques (i.e., the "staircase effect"), (7) are to some extent dependent upon the stability, dimensions and behavior of the particle "melt pool," which can determine to a great extent the porosity and surface roughness, and (8) require specialized and relatively expensive equipment (i.e., the laser printing machinery and specially processed raw materials) for manufacture, as well as highly trained operators.

The steps of designing an implant component and associated methods of manufacturing such objects using additive material technologies such as SLS and SLM/DMLS, as described herein, can include both configuring one or more features, measurements, and/or dimensions of the implant (e.g., derived from patient-specific data from a particular patient and adapted for the particular patient), manufacturing and finishing the implant. In certain embodiments, manufacturing can include making the implant component from starting materials, for example, metals and/or polymers or other materials in solid (e.g., powders or blocks) or liquid form. In addition or alternatively, in certain embodiments, manufacturing can include altering (e.g., machining) an existing implant component, for example, a standard blank implant component or an existing implant component (e.g., selected from a library), as well as post-manufacture machining and/or processing of an implant after manufacture by SLM/DMLS techniques. The manufacturing techniques to making or altering an implant component can include any techniques known in the art today and in the future. Such techniques include, but are not limited to additive as well as subtractive methods, i.e., methods that add material, for example to a standard blank, and methods that remove material, for example from a standard blank, as well as combinations thereof (i.e., using both additive and subtractive techniques on a single object). The design of an implant component can include manufacturing, for example, using CAM software and additive, subtractive and/or casting manufacturing techniques as described herein.

In various embodiments, the design of an implant component or other manufactured object may be altered or modified to accommodate advantages and/or limitations of a specific manufacturing process, such as SLM/DMLS, which may result in differing designs for a single anatomical situation (i.e., for a single patient anatomy) based on differing manufacturing methods. The various design changes, which can (but not necessarily must) have varying degrees of impact on the ultimate performance and/or reliability of the implant, can be incorporated to accommodate a wide variety of considerations, including tolerancing and dimensioning limitations of specific manufacturing methodologies and/or equipment, design limitations and/or object feature (i.e., surface and/or subsurface feature) orientation and/or shape requirements, ease of object removal from manufacturing equipment and/or fixtures, ease of removing support surfaces or other ancillary artifacts from the manufacturing processes, improvements in manufacturing performance and/or manufacturability of multiple implants and/or implant components in a single machine "run" or batch, minimizing object and/or feature deformation and/or "warpage" during and subsequent to the manufacturing process, improving the repeatability and reliability of implant manufacturing processes and methods, and/or simplifying and/or improving the implant design to facilitate substrate removal, finishing and polishing of the object.

While the manufacture of a part via SLM/DMLS often takes far less time than traditional manufacturing, it is by no means an instantaneous process. In a typical SLM/DMLS manufacturing process, the "build time" to create an object can be broken down into "primary processing" time and "auxiliary processing" time. The primary processing time (or "laser scanning time") represents the amount of time the SLM/DMLS equipment takes to create the defined object through fusing fine metallic powders together by directed laser energy. Because the build object is created in successive layers, which are often between 20 to 100 micrometers thick, a significant number of layer passes are typically required to create an object the size of a typical implant. In one exemplary SLM/DMLS setup, the defined layer thickness might be 20 micrometers, the scan spacing ("hatch distance") could be 125 micrometers, and the laser could have a laser spot size of 200 micrometers. With such settings, it can require a significant number of passes to create a single melt layer (for a 5 cm×5 cm size object layer), and over 2,500 (twenty-five hundred) successive melt layers to create a 5 cm tall object. For example, if each layer required only 2 seconds of active laser time to melt the relevant material, the exemplary embodiment would still require over 1.3 hours of active laser scanning time to create an object. Accordingly, the amount of "primary processing" or laser scanning time required to manufacture an object can be considerable.

In addition to such primary processing time, the "auxiliary processing" time (or "secondary processing") for a SLM/DMLS object "build time" is contributed by processes other than active laser scanning. Secondary processing can include a variety of factors, such as powder deposition and leveling time, chamber preparation time, preheating, cooldown, atmospheric purging and substrate/part removal and separation. While many of these factors typically occur at discrete points in the build procedure (i.e., chamber prep occurs once prior to build initiation—cool down occurs once at the end of the build, etc.), the step of powder deposition and leveling is typically repeated at each layer, and thus the requirement for this step can contribute a significant amount of time to the overall build process. In the above example, if the powder deposition and leveling step required an additional 3 seconds to perform between each level, this step could contribute an additional 2 hours to the overall "build time" of the object (or a total build time in excess of 3 hours for a single build operation).

Moreover, the various other auxiliary steps, such as chamber prep, preheating, cooling and purging, etc., could easily add significant additional time to the overall manufacturing build time. For example, various SFF manufacturing techniques can require substantial additional set-up and break-down time, such as where the manufacturing techniques include the use of pre-heated powder/liquid and/or implant manufacturing at elevated temperatures. Because controlled cooling of manufactured components can prevent object warpage and/or degradation due to atmospheric contamination (at elevated temperatures), the cooling-down period at the end of a single manufacturing run may be substantial.

In building a given object, the auxiliary processing times are often relatively inflexible, and can often be primarily based on a given type of SLM/DMLS equipment, the chosen processing technique and/or the necessary build material. The primary processing times, however, can vary extensively, depending on a wide variety of operator-selected and/or operator-controllable variables, including the number of objects being built and the object design complexity. In many cases, there can also be a direct correlation between the number of objects built in a single "run" and the amount of laser scanning time required to create each melt level. However, even where a doubling of the number of build objects increases the laser scanning time by a factor of 2, the auxiliary processing times (which can often contribute a significant portion of the overall build time) may remain relatively constant. In such a case, an increase in the number of objects built in a single "run" can increase the overall efficiency of the SLM/DMLS process by reducing the net amount of "build time" required on a per object basis.

In addition to decreasing object build time, an increase in the number of objects built in a single manufacturing run can significantly reduce the amount of component material (i.e., powdered metal material) "wasted" or unused during a manufacturing process. At the end of a SLM/DMLS manufacturing run, the entire build chamber is typically filled with unfused powdered material, which essentially encases the manufactured object which comprises laser fused powder. A greater number of built objects will generally correlate to a greater amount of fused material (which forms the individual built objects), and a commensurate reduction in the amount of unfused material contained within the chamber. Upon completion of a build run, the unused powder is typically removed from the build chamber, and can be collected in a secondary holding container for "waste" powder.

While many manufacturers claim that waste SLM/DMLS powder can be reused, the reuse of "waste" powder is generally more restricted. For example, some processes modify the unused powder to such an extent as to preclude their reuse (i.e., partially sintering of unfused powder). Other manufacturers recommend that the unused powder be reprocessed and recertified before subsequent use. Still other manufacturers recommend that reuse of waste powder be limited to certain percentage combinations (i.e., mixes) with virgin powder. Regardless of the reason and/or recommended limitations, however, because waste powder has been subjected to the build environment (which can significantly alter the size, shape and/or material characteristics of portions of the powder), the quality and characteristics of this powder may be suspect. Accordingly, such waste powder is unlikely to be directly reused for the direct manufacture of implant components for human implantation, and is likely to be discarded.

Another significant advantage to increasing the number of build objects in a given SLM/DMLS processing chamber is that, depending upon the object design and orientation/proximity of adjacent objects, it may be desirable and/or advantageous to utilize locations on one build object as an anchor and/or support for other build objects. In SLM/DMLS manufacturing, supports or other features/artifacts are typically required to anchor down certain unsupported features, to avoid shrinkage and/or "curling" of cooling and solidifying material. Such features are also often required to provide a base and/or foundation to support portions of the "melt pool" formed when the laser melts the metallic powder. While recent developments have allowed for increased geometric freedom in the angulation of such support structures (i.e., some methods allow for up to 60 degrees of off-angle support on a given structure), SLM/DMLS build objects still typically require substantial support arrangements that extend from the substrate surface to various portions of the object. To some extent, therefore, the anchoring/support requirement restricts the process of geometric freedom.

SLM Build Object "Packing" Considerations

While it may be desirous to simply increase the number of objects built in a single SLM/DMLS "run" by replicating and repeating the size and position of a given object within the build chamber (see FIG. 12), there are numerous disadvantages and limitations associated with SLM/DMLS (including those described previously) that should be considered and assessed prior to simply "packing in" multiple objects into the build chamber. For example, a selected SFF build technique may create build objects having various inherent structural limitations that could preclude and/or inhibit certain design orientations and/or limit the allowable proximity and/or spacing of adjacent objects. Similarly, the various anchoring and/or support structures required for each build object could interfere in some manner, or could result in a build platform and associated objects having such complexity that the individual build objects are difficult or impossible to remove from the substrate or each other.

Moreover, the simple packing of multiple implant component designs in a repeating pattern and orientation on a given substrate may not be an optimal method of maximizing product density, especially where the various build objects are differentially sized and/or shaped patient-specific implant components designed for a variety of different patients. Accordingly, various embodiments described herein disclose systems that employ a variety of criteria and/or boundary conditions to select, discard, reposition, reorient and/or otherwise modify datasets of implant component designs to create an optimal distribution of build objects for creation in a single SLM/DMLS build run.

In various embodiments, the orientation, placement, spacing and design of multiple patient-specific and/or patient-adapted implant components, such as femoral implant components, can be specifically chosen to maximize SLM/DMLS build chamber capacity, minimize waste powder and optimize object build flexibility while reducing and/or eliminating various manufacturing or structural limitations inherent in the SLM/DMLS build process. Desirably, such an arrangement can facilitate maximum build efficiency on a per-component basis, minimize manufacturing limitations and/or "artifacts" that may be inherent in the chosen SLM/DMLS manufacturing process, and simplify component/substrate separation and component finishing.

Collecting Patient Data

In creating and/or selecting an implant component data set for each patient, the patient-adapted (e.g., patient-specific and/or patient-engineered) implant components described herein can be selected (e.g., from a library), designed (e.g., preoperatively designed including, optionally, manufacturing the components or tools), and/or selected and designed (e.g., by selecting a blank component or tool having certain blank features and then altering the blank features to be patient-adapted). Moreover, related methods and associated guide tools, such as designs, strategies and tools for resectioning a patient's biological structure, can be selected and/or designed. In certain embodiments, patient-adapted features of an implant component, guide tool or related method can be achieved by analyzing imaging test data and selecting and/or designing (e.g., preoperatively selecting from a library and/or designing) an implant component, a guide tool, and/or a procedure having a feature that is matched and/or optimized for the particular patient's biology. The imaging test data can include data from the patient's joint, for example, data generated from an image of the joint such as x-ray imaging, cone beam CT, digital tomosynthesis, and ultrasound, a MRI or CT scan or a PET or SPECT scan, that is processed to generate a varied or corrected version of the joint or of portions of the joint or of surfaces within the joint. Certain embodiments can include methods and/or devices that create/select a desired model of a joint or of portions or surfaces of a joint based on data derived from the existing joint. For example, the data can also be used to create a model that can be used to analyze the patient's joint and to devise and evaluate a course of corrective action. The data and/or model also can be used to design an implant component having one or more patient-specific features, such as a surface or curvature.

Implant component datasets can describe articular implant components having one or more patient-specific features adapted to match one or more of the patient's biological features, such as one or more of biological/anatomical structures, alignments, kinematics, and/or soft tissue impingements. Accordingly, the one or more patient-specific features of an implant component can include, but are not limited to, one or more implant component surfaces, such as surface contours or angles, and one or more implant component dimensions such as thickness, width, depth, or length. The patient-specific feature(s) of an implant component can be designed based on patient-specific data to substantially match one or more of the patient's biological features (i.e., anatomical and/or biological features). In various embodiments described herein, the act of designing an implant component can include manufacturing the implant component having the related design features. For example, designing an implant component can include preoperatively establishing a design of one or more features of an implant component, for example, using a CAD computer program on a computer system specialized operated for such use and having one or more user interfaces, and instructing the transfer of that design data, for example, from a CAD computer program or computer system to a CAM (computer-aided manufacturing) computer program or computer system. Optionally, in certain embodiments, designing the implant can further include instructing the initiation of manufacturing the physical implant and/or manufacturing the implant.

Implant component datasets can also be obtained by analyzing imaging test data from a patient and selecting (e.g., preoperatively selecting from a library of implant components) an implant component(s) that best fits one or more pre-determined patient-specific parameters that are derived from the imaging test. Implants of various sizes, shapes, curvatures and thicknesses can be selected and/or designed and manufactured. The implant designs and/or implant components, as well as electronic datasets defining such designs and/or components, can be selected from, catalogued in, and/or stored in a library. The library can be a virtual library of implants, or components, or component features that can be combined and/or altered to create a final implant. The library can include a catalogue of physical implant components. In certain embodiments, physical implant components can be identified and selected using the library. The library can include previously-generated implant components having one or more patient-adapted features, and/or components with standard or blank features that can be altered to be patient-adapted.

In various embodiments, a dataset for an implant component can include patient-specific and/or patient-adapted features that are both selected and designed. For example, a dataset representing an implant component initially can be selected (e.g., preoperatively selected from a library of implants) to have a feature with a standard or blank dimension, or with a larger or smaller dimension than the predetermined patient-specific dimension. Then, the implant dataset can be modified so that the standard dimension or blank dimension or larger-dimensioned or smaller-dimensioned implant feature is altered to have the patient-specific dimension. In a similar manner, a dataset can include a patient-engineered implant component, in which various features incorporate one or more patient-engineered features optimized from patient-specific data to meet one or more parameters to enhance one or more of the patient's biological features, such as one or more biological/anatomical structures, alignments, kinematics, and/or soft tissue impingements. Accordingly, the one or more patient-engineered features of an implant component can include, but are not limited to, one or more implant component surfaces, such as surface contours, angles or bone cuts, and dimensions such as thickness, width, depth, or length of one or more aspects of the implant component. The patient-engineered feature(s) of an implant component can be designed and/or manufactured (e.g., preoperatively designed and manufactured) based on patient-specific data to substantially enhance or improve one or more of the patient's anatomical and/or biological features. Methods for preparing certain patient-engineered features are described, for example, in U.S. Ser. No. 12/712,072, entitled "Automated Systems For Manufacturing Patient-Specific Orthopedic Implants And Instrumentation" filed Feb. 24, 2010, which is incorporated herein by reference.

If desired, implant component designs can include one or more features that are engineered to optimize or enhance one or more of the patient's biological features, for example, (1) deformity correction and limb alignment (2) preserving bone, cartilage, and/or ligaments, (3) preserving and/or optimizing other features of the patient's anatomy, such as trochlea and trochlear shape, (4) restoring and/or optimizing joint kinematics or biomechanics, and/or (5) restoring and/or optimizing joint-line location and/or joint gap width. In various embodiments, a plurality of implant designs can be designed and/or selected for a single patient and/or surgical procedure, with each design desirably accomplishing various combinations of differing or competing objectives.

Once one or more datasets describing desired implant designs or a patient have been designed and/or selected, the dataset reflecting these designs can be forwarded or otherwise transferred to a database, library or other electronic system for further processing. In various embodiments, implant datasets can include surface data in addition to or in place of voxel or volumetric data. An implant surface model, for example, can be loaded as a mesh surface (e.g. in an STL file) or a parametric surface (e.g. in an IGES file) without conversion to volumetric voxel data. The implant surface can be derived from a variety of sources, including from CAD files and/or from medical image data (e.g. CT data) using, for example, a marching cubes or isosurface algorithm, resulting in a surface dataset.

SLM Manufacturing

FIG. 1 depicts a schematic view of equipment and the process used in a typical SLM manufacturing process. SLM is a powder bed 8 process that begins with the deposition of a thin layer of powder onto a substrate 30, which can be disposed on a processing table 11. A high power laser 6 scans the surface of the powder, generating heat that causes the powder particles to melt (see melted powder 7) and form a melt pool which solidifies as a consolidated layer of material. Once the layer has been scanned and relevant portions melted/solidified, another layer of powder is deposited, which is then subsequently scanned and melted/solidified to form the next layer of the part. This process continues with multiple layers 13 until enough layers of material have been deposited/melted/solidified to create a desired object 9. Powder particles that are not melted remain loose and are removed (and can typically be reused) once the component is complete.

Automated and Semi-Automated Object Packing

Various embodiments described herein include the use of automated and/or semi-automated systems and programs to evaluate the shape of a plurality of implant component data files and plan the manufacture of build objects within a single build chamber of SLM/DMLS manufacturing equipment. The various packing arrangements described herein, as well as the different methods and/or designs that facilitate such planning and/or manufacture, can result in a significant increase in the throughput and quality of SLM/DMLS manufactured orthopedic implant components, as well as a significant reduction in per-unit cost. Relevant orthopedic implant components can include femoral implants, although a wide variety of orthopedic implant components, as well as combinations of components for a variety of joints or other anatomical structures in a single manufacturing run (i.e., femoral, tibial and patellar implant components for a single patient or multiple patients, or combinations of hip and knee implant components), can be manufactured using various methods described herein.

Various embodiments of the systems and methods described herein, as well as the implants, guide tools, and related methods of designing (e.g., designing and making) and using the implants and guide tools, can be applied to any joint including, without limitation, a spine, spinal articulations, an intervertebral disk, a facet joint, a shoulder, an elbow, a wrist, a hand, a finger, a hip, a knee, an ankle, a foot, or a toe joint. Furthermore, various embodiments described herein can encompass and/or apply to the design, selection and/or manufacture of standard and/or modular implants and/or implant components, if such are appropriate to a given patient's anatomy, as well as associated guide tools.

In various embodiments, a method of manufacturing implant components can include querying a database containing a plurality of implant component datasets, each dataset defining the three-dimensional shape (or other pertinent information) of an individual implant component. From the database, the program can evaluate, identify, select and/or deselect relevant datasets for potential inclusion into a prospective "object build run" in a processing chamber of SLM/DMLS manufacturing equipment. In additional to three-dimensional ("3D") and/or two-dimensional boundary shape data of the pertinent implant component, the dataset will also desirably include information regarding acceptable structural component materials and volumetric condition of the implant component (i.e., internal structural details of the component such as the existence of a solid or hollow internal structure, etc.). Various additional data regarding the component can be included in the individual dataset, including information such as (1) desired date of component manufacture and/or manufacturing priority, and (2) desired and/or undesired orientations and/or alignments of the component within the build chamber. Once a plurality of pertinent datasets has been selected for potential inclusion into a desired build run, a computer can virtually position one or more of the selected datasets within a representative volume of the intended SLM/DMLS build chamber, and analyze various permutations and combinations of different locations, orientations and/or selections of the datasets to determine whether the selected datasets can all be included within the build chamber without overlapping or otherwise conflicting in an unacceptable fashion.

In various embodiments, the datasets or implant surface models thereof can be compared, for example, by calculating intersections between the surfaces of adjacent implant datasets. The models can be used to detect interference between any adjacent object volume and/or a boundary volume of the virtual build chamber. In various embodiments, implant model triangulation points can be transformed onto an image volume space to obtain a binary representation of the implant. The binary structure then can be manipulated (e.g., dilated and eroded using voxel balls having pre-set diameters) to obtain a solid field mask. The solid field mask can be compared against the occupied and/or unoccupied space within the virtual build chamber, to identify interfering object volumes. In this way, interfering object volumes and non-interfering object volumes can be determined (e.g., using Matlab ISOSURFACE function), for example, using representative colors or some other distinguishing features in a model. If desired, the resulting model image can be rendered on a virtual rendering canvas (e.g., using Matlab GETFRAME function) and saved onto a computer-readable medium.

If all of the selected datasets can be accommodated in the representative volume, the computer may choose to select an additional dataset and conduct various permutations (as previously described) to determine if the additional dataset can be accommodated in the representative volume. If so, the program may choose to select another dataset, and repeat the assessment process.

If one of more of the selected datasets can not be accommodated in the representative volume, the computer may choose to deselect one or more datasets and conduct various permutations (as previously described) to determine if the remaining datasets can be accommodated in the representative volume. If not, the program may choose to deselect another dataset, and repeat the assessment process.

Once a desired number of permutations has been completed and/or once the representative volume is deemed sufficiently packed, the system may initiate a request for human-operator review of the intended build plan, or alternatively, the program may load or otherwise transmit the build plan to the appropriate SLM/DMLS manufacturing equipment. The program may also notify the dataset database that the selected datasets have been selected for manufacture, to ensure that the relevant dataset will not inadvertently be included in another object build run. This notification could include identifying the relevant stage of manufacture (i.e., "component manufacture initiated") to interested parties including scheduling and manufacturing personnel, shipping personnel, the surgeon and potentially even the patient.

Manual and Semi-Manual Object Packing

Various alternative embodiments described herein include the use of manually-operated and/or semi-automated systems and programs to evaluate the shape of a plurality of implant component data files and plan the manufacture of build objects within a single build chamber of SLM/DMLS manufacturing equipment. The various packing arrangements described herein, as well as the different methods and/or designs that facilitate such planning and/or manufacture, can result in a significant increase in the throughput and quality of SLM/DMLS manufactured orthopedic implant components, as well as a significant reduction in per-unit cost. Relevant orthopedic implant components can include femoral implants, although a wide variety of orthopedic implant components, including combinations of components for a variety of joints or other anatomical structures in a single manufacturing run (i.e., femoral, tibial and patellar implant components for a single patient or multiple patients, or combinations of hip and knee implant components), can be manufactured using the various methods described herein.

In various embodiments, 2D or 3D representations of an implant (i.e., dataset) can be selected from a database of implant designs scheduled for manufacture, and the implant representation can be merged into a common coordinate system. The representation of the implant can be rendered into a 3-D image, for example application programming interfaces (APIs) OpenGL® (standard library of advanced 3-D graphics functions developed by SG), Inc.; available as part of the drivers for PC-based video cards, for example from www.nvidia.com for NVIDIA video cards or www.3dlabs.com for 3Dlabs products, or as part of the system software for Unix workstations) or DirectX® (multimedia API for Microsoft Windows® based PC systems; available from www.microsoft.com). The 3-D image can be rendered showing the implant from varying angles, e.g., by rotating or moving it interactively or non-interactively, in real-time or non-real-time.

The software can be designed so that the operator can select the implant and project it or drag it onto a virtual canvas or other location representation a projected build chamber, substrate and/or other manufacturing feature, using suitable tools and techniques. The operator can desirably move and rotate the implant in three dimensions relative to the build chamber, and can perform a visual inspection of the fit between the implant and the build chamber. The visual inspection can be computer assisted, and can include the use of an automated and/or semi-automated interference algorithm to identify areas where the representation overlaps or otherwise conflicts with other implants and/or features of the build chamber. The system can also include limiters or other boundary conditions that prevent or limit the operator from manipulating an object in violation of various conditions of the dataset, such as inhibiting spherical rotation of an implant but allowing "flipping" of the implant to ensure proper alignment of melt pool layers and/or build lines. The procedure can be repeated until a satisfactory fit for the implant within the build chamber has been achieved. The procedure can be performed manually by the operator; or it can be computer assisted in whole or part. For example, the software can select a first implant that the operator can test. The operator can evaluate the fit. The software can be designed and used to highlight areas of poor alignment between the implant and surrounding features. Based on this information, the software or the operator can modify the implant location and/or orientation, or can deselect the current dataset and select another implant dataset and test its alignment. One of skill in the art will readily be able to select, modify and/or create suitable computer programs for the purposes described herein.

In various alternative embodiments, the implant and virtual build chamber can be visualized using one or more cross-sectional 2D images. Typically, a series of 2D cross-sectional images will be used. The 2D images can be generated from dataset information using methods and tools known to those of skill in the art. The implant can then be superimposed onto one or more 2-D images of the virtual build chamber. The 2-D cross-sectional images can be reconstructed in other planes, e.g., from sagittal to coronal, etc. Isotropic data sets (e.g., data sets where the slice thickness is the same or nearly the same as the in-plane resolution) or near isotropic data sets can also be used. Multiple planes can be displayed simultaneously, for example using a split screen display. The operator can also scroll through the 2D images in any desired orientation in real-time or near-real-time; the operator can rotate the images while doing this. The implant can be displayed in cross-section utilizing different display planes, e.g., sagittal, coronal or axial, typically matching those of the 2-D images demonstrating the virtual build chamber. Alternatively or in addition, a three-dimensional display can be used for creating the build plan. The 2D electronic image and the 2D or 3-D representation of the articular repair system can be merged into a common coordinate system. The implant can then be placed at the desired location and/or orientation within the virtual build chamber. The series of 2D cross-sections of the virtual build chamber, the implant and any pre-assigned implant structures can be displayed interactively (e.g., the operator can scroll through a series of slices) or noninteractively (e.g., as an animation that moves through the series of slices), in real-time or non-real-time.

In various embodiments, the fit between the selected implant, pre-assigned implants and the virtual build chamber can be evaluated. If desired, additional unselected implants resident in the database (for potential build scheduling and/or inclusion in the build run) can be displayed to the operator, and the system can suggest or recommend alternative implant components automatically and/or upon request of the operator.

The various implants for assignment and manufacture in a single build run (and within a single build chamber) can include implants of a range of different dimensions, sizes, shapes and thicknesses for a variety of patients. Different dimensions, sizes, shapes and thicknesses can be available for a medial condyle, a lateral condyle, a trochlea, a medial tibia, a lateral tibia, the entire tibia, a medial patella, a lateral patella, an entire patella, a medial trochlea, a central trochlea, a lateral trochlea, a portion of a femoral head, an entire femoral head, a portion of an acetabulum, an entire acetabulum, a portion of a glenoid, an entire glenoid, a portion of a humeral head, an entire humeral head, a portion of an ankle joint, an entire ankle joint, and/or a portion or an entire elbow, wrist, hand, finger, spine, or facet joint.

In various embodiments, a plurality of packing arrangements can be created by the system, and each packing arrangement assessed using a variety of assessment metrics. Such metrics could potentially include (1) selecting one or more implant data sets from a database containing a plurality of implant data sets, (2) achieving a desired number of manufactured objects in a given build run, (3) accommodating priority or non-priority status in scheduling of the manufacture of various implant components (i.e., "forcing" the inclusion of critical components), (4) accommodating similarities and/or differences in design of given implant components (i.e., height, width, complexity and/or volume of one or more components), (5) accommodating manufacturing process requirements (i.e., differing laser power and/or powder sizes may be desired for manufacturing an articulating femoral implant component as opposed to a tibial tray anchor), and (6) accommodating differing implant components for a single surgery in a single build (i.e., building the tibial, femoral and patellar components for an individual patient in the same build).

Packing Methodology

There are a wide variety of computational methods that an automated program can employ in filling the representative volume with object datasets. In computation complexity theory, the "bin packing problem" is a combinatorial NP-hard problem. The problem includes object of different shapes and/or volumes, and these objects are packed into a finite number of bins of in a way that desirably minimizes the number of bins used.

There are many variations in the "bin packing problem," which can include 2-dimensional packing, linear packing, packing by weight, packing by cost, etc. Such problems can be applied to a wide variety of applications, including filling up shipping containers, loading trucks having specified volumes and/or weight capacities and/or creating file backups for electronic storage media.

There are various sophisticated algorithms that can be employed to optimize solutions to a typical "bin packing problem." In addition, various heuristics have been developed, such as the "first fit algorithm," to provide solutions that, while non-optimal in many cases, can be specifically tailored to be made more effective when applied to a given packing situation (i.e., such as sorting the order of items by size or volume in decreasing order). Additional exemplary algorithms can include the "best fit decreasing" and/or "first fit decreasing" strategies. A particularly useful algorithm for packing arbitrary geometric shapes is contained within a graduate school thesis entitled "Geometric Bin Packing Algorithm for Arbitrary Shapes," written by Arfath Pasha for the University of Florida, and publicly available at the following web address: http:/cimar.mae.ufl.edu/CIMAR/pages/thesis/Pasha_A_CISE.pdf, the disclosure of which is incorporated herein by reference in its entirety.

The optimal packing of object datasets into a representative build chamber volume and their subsequent manufacture via SLM/DMLS presents a unique challenge to the "bin packing problem." Because SLM/DMLS manufacturing relies upon a "melt pool," it is typically desirable that the manufactured objects be separated by a defined space or boundary. Such separation can prevent adhesion or combining of the individual melt pools, which in extreme cases could cause the individual objects in a single run to become admixed and/or subject to unwanted or undesirable deformation.

In various embodiments, the systems and methods described herein can include a "spacing factor" or other modification to the individual datasets to ensure that the packing algorithm produces an intended build plan that includes sufficient spacing between individual objects. In one embodiment, the modification can comprise a global increase in the dimensions of the object contained within a given dataset, such as an increase in the outer dimensions of the object by 1 mm in all directions. The packing algorithm can then be applied to the modified dataset(s) as previously described. Once an optimal build plan has been obtained, the object dimensions can be reduced accordingly and/or the original object dimensions can be substituted into the build plan. In this manner, an optimal build plan with a minimum of a 2 mm spacing between adjacent objects (due to the 1 mm size increase for each object) can be created.

Orientation and/or Alignment Considerations

Because various SFF manufacturing methods involve the creation of a thin melt pool layer laid down via multiple tracks in a generally linear fashion, and subsequent melt pool layers are build on top of one another in a sequential fashion, this manufacturing method can result in objects having anistotropic material properties that are highly directional and orientation-dependent (i.e., relating to the scanning direction and/or other factors). For example, crack propagation may tend to follow inter-layers boundaries, and analysis of destruction samples may show a combination of brittle and ductile fractures. Solidification microstructure of SLM/DMLS parts generally determines the strength properties, and the solidification microstructure essentially depends on the local solidification. Moreover, notable thermal stresses may exist in SLM/DMLS parts because of the large temperature gradients caused by the rapid cooling during the SLM/DMLS processing. In addition, SLM/DMLS parts may have a greater level of elasticity within an individual layer than between layers, which may result in crack propagation and/or cleavage at layer contacts.

Figure 7:
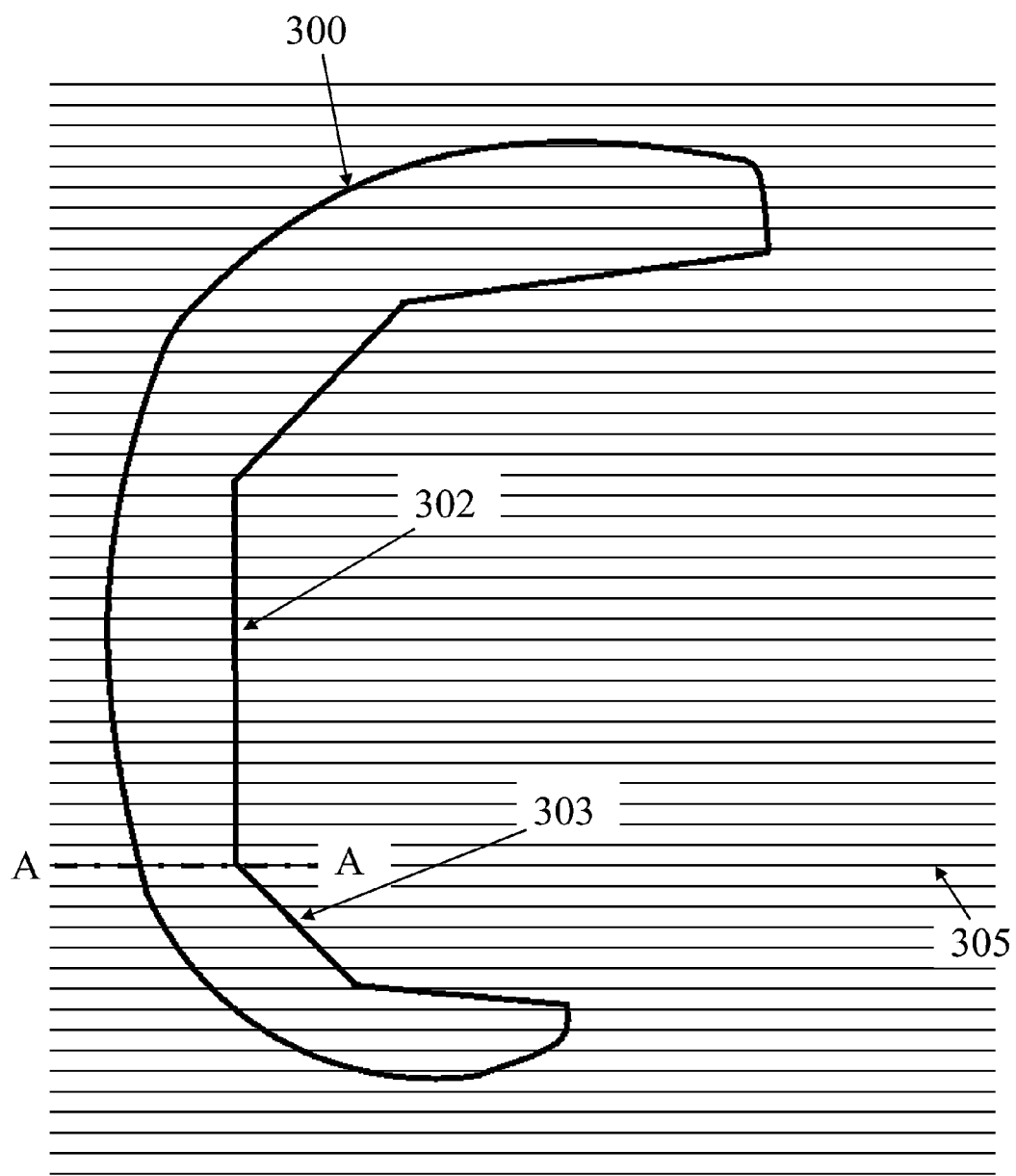
FIG. 7 depicts a cross-sectional view of one exemplary embodiment of an implant design and manufacturing orientation.

In various embodiments, the design and/or orientation of an implant may be a significant consideration due to various features of the manufacturing method(s). The anisotropic nature of objects manufactured using SLM/DMLS should be assessed during the evaluation and/or "packing" of datasets within a virtual build chamber. Depending upon object design, there may be a significant "window" of desired and/or undesired object orientations relative to the scanning direction, layer direction and/or other direction that can result in an unintended localized weakness and/or other undesirable results in the implant. For example, FIG. 7 depicts a cross-sectional view of one exemplary embodiment of an implant design and manufacturing orientation that, in some embodiments, could potentially create undesired localized weaknesses. The implant 300 has been manufactured using a SLM/DMLS process, with a plurality of horizontal layers (shown as the parallel horizontal lines in the figure, which is a greatly simplified representation of the numerous layers used to create the implant) representing the SLM/DMLS manufacturing process. One region that could potentially be prone to undesirable fracture and/or failure could be a portion of the implant in the vicinity of region A-A, which includes a region where the minimum implant thickness (at a planar boundary between planar surfaces 302 and 303) approximately meets a horizontal layer 305 created during the SLM/DMLS manufacturing process. Depending upon localized loading conditions and various structural considerations, this area might experience a relatively high level of stress during use after implantation that could, in some embodiments, result in fracture or other implant failure, due to the lower material thickness, geometric artifacts that can affect implant strength and/or fracture resistance (i.e., notch sensitivity) and localized weaknesses from the selected manufacturing process. In such a case, it could be desirous to modify one or more of these factors during implant manufacture to reduce the fracture potential in this area, if such regions were significantly weaker than desired for the implant's intended application.

Figure 8:
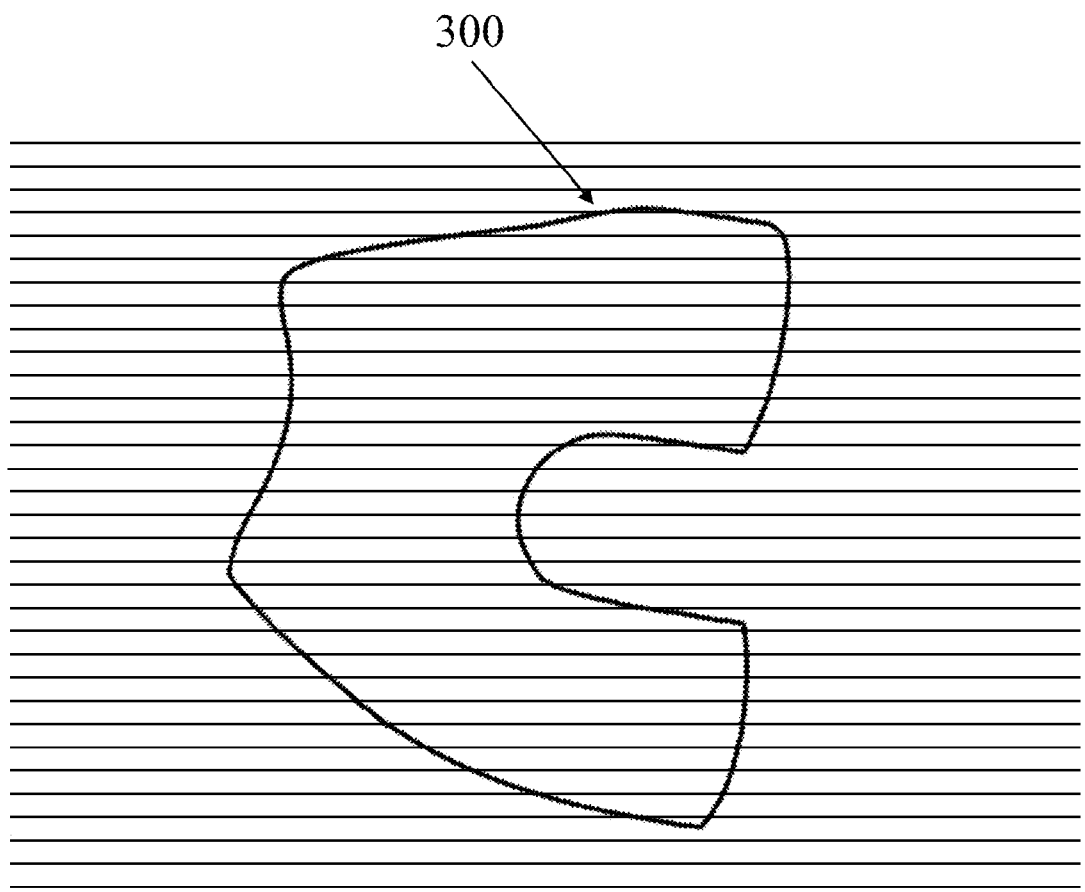
FIG. 8 depicts a side view of the implant of FIG. 7 with a modified manufacturing orientation.

In contrast, FIG. 8 depicts a side view of the implant of FIG. 7, with a modified manufacturing orientation that desirably results in a decreased likelihood of implant failure along a given manufacturing layer (as compared to the embodiment of FIG. 7). The implant 300, which has been manufactured using a SLM/DMLS process, incorporates a plurality of horizontal layers (shown as the parallel horizontal lines in the figure, which is a greatly simplified representation of the numerous layers used to create the implant) representing the SLM/DMLS manufacturing process. In such a case, it may be possible to decrease the local implant thickness in various regions and/or further optimize the orientation of the implant during manufacture to reduce any fracture potential. By incorporating potentially weaker areas of the implant along the longitudinal axis of the condylar portions, the present embodiment may be less likely to fail, may reach acceptable strength levels for a given application and/or may be designed to fail in less critical regions.

In various of the embodiments described herein, an implant dataset can include information regarding desired and/or undesired SLM/DMLS manufacturing orientations, which may be utilized by an automated or semi-automated program (and/or by a manual operator) during development of a SLM/DMLS build plan. The manufacturing orientation information can include one or more mandatory build orientations and/or orientation ranges, such that the packing algorithm and/or other process only evaluates the object within a certain range of orientations. In addition or alternatively, the implant dataset can include information regarding unacceptable and/or suboptimal SLM/DMLS manufacturing orientations, which can be utilized by an automated or semi-automated program (and/or by a manual operator) during development of a SLM build plan to exclude and/or prefer one or more build orientations and/or orientation ranges.

Some significant features of various embodiments described herein include various methods, techniques and/or processes to align, orient and/or otherwise position implants or other objects to be manufactured relative to a known reference plane, reference axis, "home" or "zero" location and orientation of the SLM/DMLS manufacturing equipment or portions thereof (i.e., the laser source, the scanning mechanism and/or scanning path). Consistent orientation and location relative to known positions, alignments and/or orientations can facilitate the reliable and repeatable manufacturing of implant components in a single machine and/or across multiple machines, and can further assist with identification and/or alleviation of process and/or design defects discovered during or after the manufacturing process. Moreover, proper alignment and/or location of a manufactured object relative to the manufacturing machinery can potentially allow a designer and/or operator to predict and/or accommodate for various manufacturing advantages and/or disadvantages inherent in the chosen manufacturing processes.

In various embodiments, the electronic datasets and/or design files described herein, such as a CAD file, for a knee implant component (in this example, a "total knee" implant component for replacing femoral surfaces) can be loaded into a database and selected for virtual packing into a build chamber of SLM/DMLS processing equipment or otherwise accessed to facilitate manufacture of the component by the SLM/DMLS equipment. The CAD design file can include a wide variety of information about the component, including desired outer surfaces for the implant. In one embodiment, the implant design can include information regarding various surfaces and/or other features of the implant, one or more of which can be designated as "reference parameters" for use in aligning and/or positioning the design and/or object relative to the SLM/DMLS equipment.

Figure 2A:
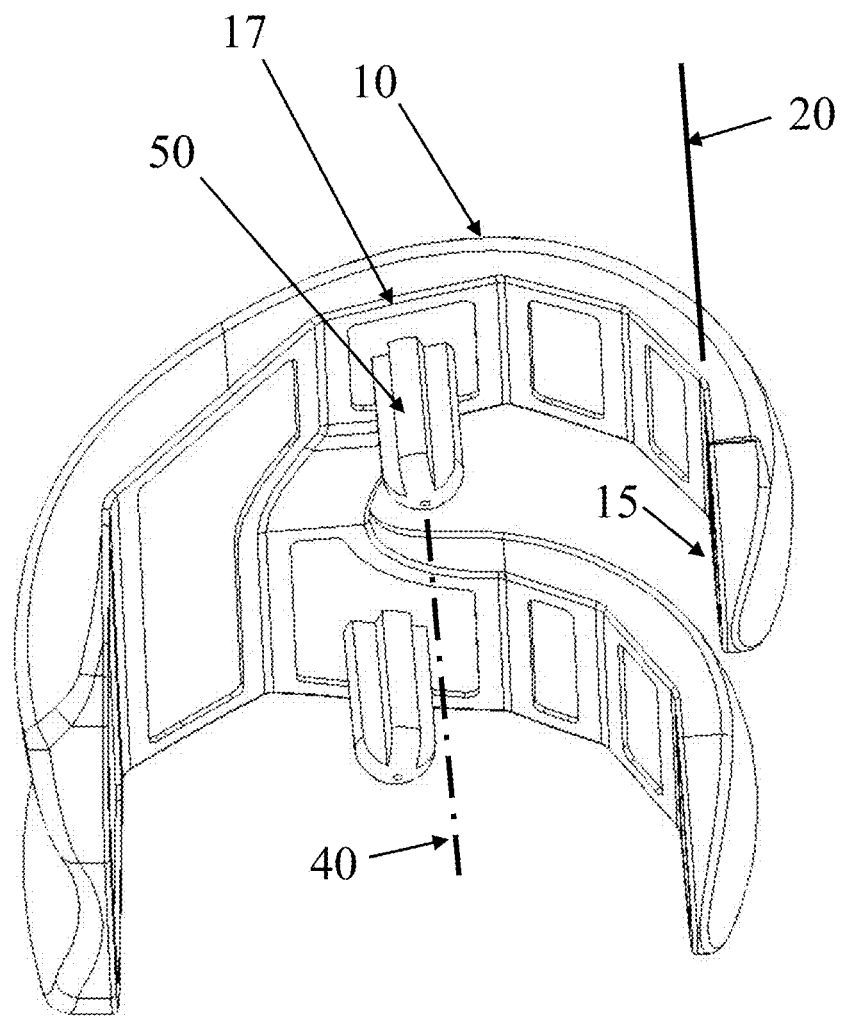
FIG. 2A depicts a perspective view of one embodiment of a femoral component for a "total knee" implant.
Figure 2B:
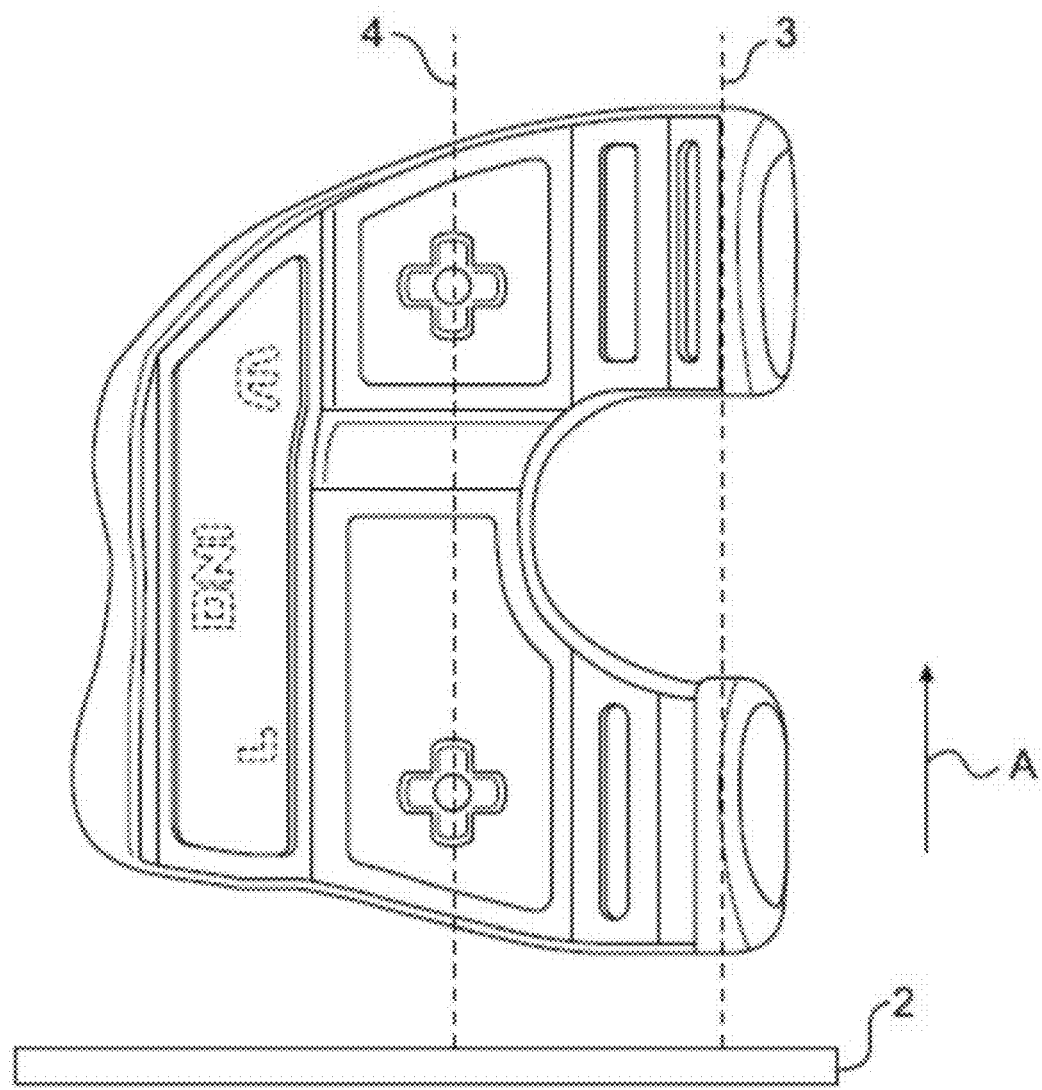
FIG. 2B depicts one exemplary alignment configuration for the component of FIG. 2A.

For example, in manufacturing a femoral component of a "total knee" implant, one embodiment (shown in FIG. 2A) includes the designation of a bone-facing implant surface 15 on a medial condylar portion 10 (i.e., facing a posterior bone cut on the medial condyle) of the implant as a first reference datum 20. This first reference datum 20 will desirably be aligned perpendicular to the object support structure or substrate 30 (see FIG. 1) that supports the object during the manufacturing process. In addition, the embodiment further includes the designation of a second reference datum 40, which can be a longitudinal axis of a support peg 50 or stem on the medial condylar portion 10 of the implant, which can be aligned parallel to the object support structure or substrate 30. Alternatively, the second datum could be determined using a distal bone-facing surface 17 of the implant, which can be aligned perpendicular to the object support structure or substrate 30. Designation of at least two datum 20 and 40 desirably define an orientation relative to the SLM/DMLS equipment. In alternative embodiments, the datum may be aligned relative to the laser, the powder depositor and leveler, the powder bed, the processing table, the line of action of gravitational forces, or other relative measures. In various embodiments, one or more additional datum such as one or more known positions (i.e., one or more implant component positions, such as points where the post meets various implant surfaces) could be employed to further define object location and/or orientation. Another exemplary alignment configuration, using a bone facing surface of the medial condylar portion and an internal axis passing through the support pegs, is shown in FIG. 2B.

In various embodiments, the identification and employment of such datum in conjunction with SLM/DMLS manufacturing equipment can ensure consistency throughout multiple "runs" of manufactured implants (in the same or different machines) and can significantly reduce time and/or effort (and possibly obviate a need for human intervention) required for "set up" of an individual SLM/DMLS machine for creating a given implant design. Moreover, because various properties of the implant and its component material(s) can potentially be dependent upon the direction and/or orientation of the implant feature(s) being created by the SLM/DMLS equipment, due to a wide variety of factors, information regarding the proposed alignment of the object may be highly relevant to the implant manufacture.

By choosing relative measures for alignment (i.e., bone-facing planar surfaces of the implant), the present embodiment defines a repeatable and easily accessible alignment technique useful in packing patient specific implants into a virtual build chamber. Such files can include implants of differing sizes and/or shapes to be manufactured via SLM/DMLS techniques, which allow the designer and/or a computer program to anticipate, accommodate and/or assess various manufacturing considerations, limitations and/or advantages in designing, positioning and/or orienting the implant for manufacture.

FEA Analysis

Various embodiments disclosed herein will desirably include a FEA or other analysis of relevant implant datasets, which optionally may include analyses of material property information particular to the type of manufacturing processes as well as the design and/or orientation of the implant (as oriented and positioned in the intended build plan). Such an analysis can occur immediately prior to SLM/DMLS manufacture (i.e., FEA analysis of each object in the build plan, with relevant manufacturing and orientation data, can be evaluated) or the analysis may be conducted on some subset thereof at any point in the evaluation and virtual packing process. The FEA analysis will desirably identify and/or highlight one or more locations of high stress and/or areas of localized implant weakness, including those that may be particular to the type of manufacturing processes as well as the design and orientation of the implant. Where FEA analysis of a part design and/or orientation identifies one or more regions of potential weakness and/or failure, it may be desirous to reposition and/or reorient the object in the build plan (and/or may necessitate repacking of the build plan on some manner).

The maximum principal stress observed in FEA analysis can be used to establish an acceptable minimum implant thickness for an implant component having a particular size and, optionally, for a particular patient (e.g., having a particular weight, age, activity level, etc). In certain embodiments, an implant component design or selection can depend, at least in part, on a threshold minimum implant component thickness. In turn, the threshold minimum implant component thickness can depend, at least in part, on patient-specific data, such as condylar width, femoral transepicondylar axis length, and/or the patient's specific weight. In this way, the threshold implant thickness, and/or any implant component feature, can be adapted to a particular patient based on a combination of patient-specific geometric data and on patient-specific anthropometric data. This approach can apply to any implant component feature for any joint, for example, the knee, the hip, or the shoulder.

In various embodiments, the design of a given implant component and/or various features therein can be further assessed and/or modified by including FEA modeling and/analysis, either alone or in combination with information relating to the specific manufacturing method chosen for creating the implant. For example, the creation of an implant using SLM/DMLS manufacturing methods may produce an implant having differing density, porosity, durability, fatigue strength and/or other material properties than those of an implant created through traditional casting techniques. A finite element analysis (FEA) of an SLM/DMLS implant and/or intended implant design may identify areas of the implant/design prone to increased and/or excessive loads, which may induce the designer to modify the design to better accommodate the anticipated loading (i.e., increase the local or global implant thickness and/or alter implant geometry or location of planar surfaces). If desired, such an FEA analysis may identify areas of concern that may impel a redesign of the implant to alleviate strength and/or durability concerns. Moreover, such a redesign of the implant may compel a redesign and/or reassessment of a given build and/or packing plan.

In a similar manner, an FEA analysis may identify areas of one or more build objects that could benefit from some modification of the intended manufacturing process at one or more times part-way through the manufacturing process (i.e., "cross-hatching" or remelting an individual portion of a melt layer to reduce/avoid the formation of interconnected porosity and/or buckling deformation in a localized manner), and then continuing the layer deposition and laser melting process to complete the implant manufacture. If desired, the material properties (and/or potentially one or more component materials) of an implant can be varied to accommodate unique or localized requirements. For example, it may be desirable for the porosity and/or tensile strength/elasticity of a material in a femoral implant component to vary along the surface or cross-sectional profile of the implant. In a similar manner, it may be desirous for a surface of such an implant to posses differing mechanical properties than subsurface portions of the implant. Likewise, it may be desirous for a periphery of such an implant to posses differing mechanical properties than central portions of the implant. In such a case, it may be advantageous to alter the material properties of such an implant in some manner, such as by altering the laser speed, power, duration and/or remelting one or more melt layers (or specific sections of an individual melt layer) to accommodate the varying demands placed upon the implant. Alternatively, the implant may comprise various materials that are adhered, layered or otherwise arranged in some fashion, including the use of multiple types of materials and/or material properties in non-aligned layers (i.e., a composite-like layering materials), to accomplish various objectives of the present disclosure.

In a similar manner, implants comprising metals and/or ceramic constituents may be formed of two or more materials, or may comprise a single material with sections or portions having varying material characteristics (i.e., by radiation, heating, cooling, hipping, annealing, chemical action, work hardening, peening, carburizing, hardening, surface treating, oxidation, etc.) For example, the medial and/or lateral and/or superior and/or inferior portions of a tibial tray inset maybe formed from two or more materials adhered or otherwise connected in some manner, each material having a unique material property, resulting in an implant with differing mechanical properties on its medial and/or lateral and/or superior and/or inferior sides. Such an implant could alternatively comprise a multi-layered material, with different materials and/or material properties exposed on the surface during a subsequent machining process (with the processing tools extending to differing depths), thereby resulting in a generally uniform layered material with different surface properties on the surface of its medial and lateral sides.

Supports, Anchors and Adjusting for Characteristics of the Manufacturing Process In various embodiments, the design of an implant component and/or the manufacturing plan (also referred to as "build plan") may be altered or modified to accommodate advantages and/or limitations of a specific manufacturing process (e.g., SLS, SLM, EBM, etc.), which may result in differing designs for a single anatomical situation (i.e., for a single patient anatomy) based on differing manufacturing methods. The various design changes, which may have varying degrees of impact on the ultimate performance and/or reliability of the implant, can be incorporated to accommodate a wide variety of considerations. Such considerations may include, for example, tolerancing and dimensioning limitations of specific manufacturing methodologies and/or equipment; need for support of features during and/or subsequent to the manufacturing process; design limitations and/or object feature (i.e., surface and/or subsurface feature) orientation, thickness, and/or shape requirements; ease of object removal from manufacturing equipment and/or fixtures; ease of removal of support surfaces or other ancillary artifacts from the manufacturing processes; improvements in manufacturing performance and/or manufacturability of multiple implants and/or implant components in a single machine "run" or batch; minimizing object and/or feature deformation and/or "warpage" during and/or subsequent to the manufacturing process; improving the repeatability and reliability of implant manufacturing processes and methods; and simplifying and/or improving the implant design to facilitate finishing and polishing of the implant.

Figure 3:
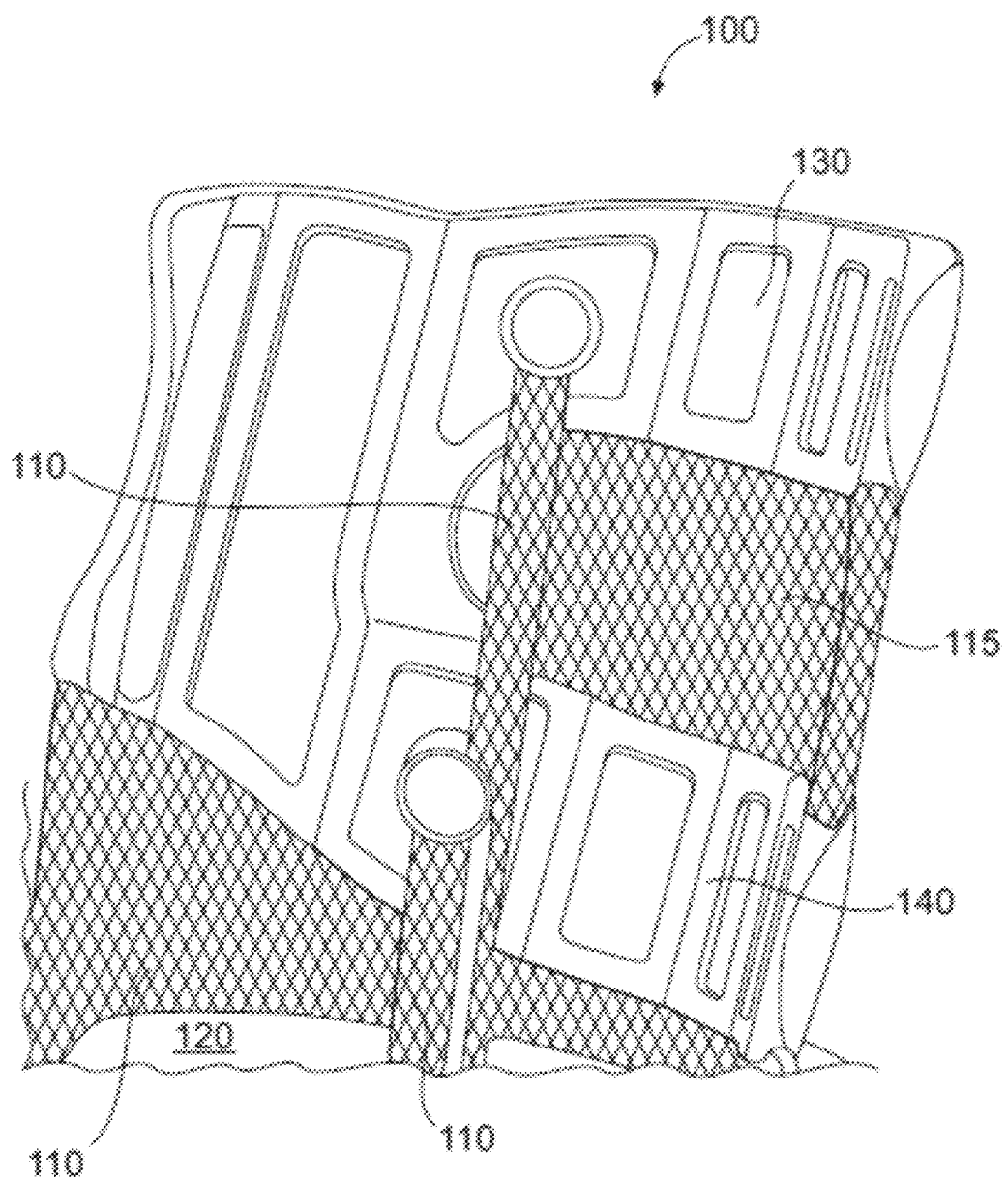
FIG. 3 depicts a perspective view of one alternative embodiment of a femoral implant component manufactured using a SLM/DMLS manufacturing process.

For example, many SFF manufacturing processes can require and/or prefer the use of support structures during the build process. In many cases, at least a portion of the component's initial design geometry cannot stand on its own, or the material requires support during melt and/or curing. In addition, the use of support structures may desirably anchor the manufactured object within the manufacturing equipment, which may prevent the object from uncontrolled movement and/or rotation/displacement during the manufacturing process, which could potentially ruin and/or degrade the quality of the part. FIG. 3 depicts one exemplary embodiment of a femoral implant 100 in which a series of support structures 110 were incorporated during the SLM manufacturing process. The support structures 110 extend between a support plate or substrate 120 and the implant 100. Additional support structures 115 extend between the medial condylar portion 130 and the lateral condylar portion 140 of the implant 10.

In various embodiments, identification of a need for and location of supporting structures can be automated (e.g., software controlling the SLM machine may automatically add supporting structures to the build plan based on information including the physical geometry of the implant design, properties of the specific powder material to be used, etc.), semi-automated (e.g., software provides suggestions of recommended supporting structures, which an operator may accept, modify, or reject prior to commencement of building), and/or manual (e.g., an operator of the SLM machine directly adds support structures to the build plan). In some embodiments, it may be advantageous to modify the design of the implant and/or the build alignment (as discussed in the ALIGMENT AND ORIENTATION section above) in order to minimize the amount of support structures needed. Decreasing the amount of supporting structures may expedite polishing of the implant.

In some circumstances, characteristics/limitations of the particular manufacturing process may result in production of a physical implant that includes localized portions which deviate from the implant design. For example, a surface of the physical implant may include one or more portions that are bulged, depressed, or otherwise diverging from an intended relative location, geometry, and/or radius of curvature. Such localized deviations from the design may arise from one or more of a variety of characteristics/limitations of the particular manufacturing process. For example, localized deviations in an implant manufactured by SLM may be the result of one or more of: lack of sufficient support; shrinkage and/or "curling" of solidifying material; material vaporization and/or spatter generation due to high heat input; variations in particle melting, melt pool stability, and re-solidifying mechanisms; "track instability" and/or "breaking up" of tracks associated with the formation of agglomerates and/or pores in the surface; and software, electrical, and/or mechanical malfunctions in the SLM system.

In various embodiments, localized deviations may be identified by analysis of an implant actually built according to the design and manufacturing plan and/or predicted according to calculations, simulations, and/or models derived from information including the implant design, parameters of the manufacturing process, and/or analysis of implants previously manufactured by the same process from other designs. Such identification of localized deviations may be automated (e.g., accomplished by design software and/or software controlling the SLM) and/or manual (e.g., accomplished by an implant designer and/or operator of the SLM machine). Once one or more localized deviations have been identified, the implant design and/or the build plan can be modified in order to compensate for the localized deviations, and a modified design and manufacture process can be implemented. In some embodiments, the magnitude of the localized defect may be defined and then utilized to determine the magnitude of the modification to the design and/or build plan that is needed.

In some embodiments, localized deviations may be compensated for by adjusting the alignment/orientation (as discussed in the ALIGNMENT AND ORIENTATION section above) of the implant relative to the SFF manufacturing equipment and/or build direction. In such embodiments, modifying alignment/orientation of the implant may, for example, result in some features of the implant being provided with additional support during the build process, which may eliminate local deviations in those features that were caused by a lack of sufficient support. Additionally or alternatively, in some embodiments, localized deviations may be compensated for by strategically adding or subtracting material in the implant design. For example, if a localized deviation involves material bulging in a region, the original implant design can be modified to include a relative depression (i.e., a subtraction of material at that location) of a magnitude related to the magnitude of the bulge. Conversely, if the localized deviation in question is a depression in the surface of the implant, the original implant design can be modified to include a relative bulge (i.e., an addition of material at that location) of a magnitude related to the magnitude of the depression.

Figure 4:
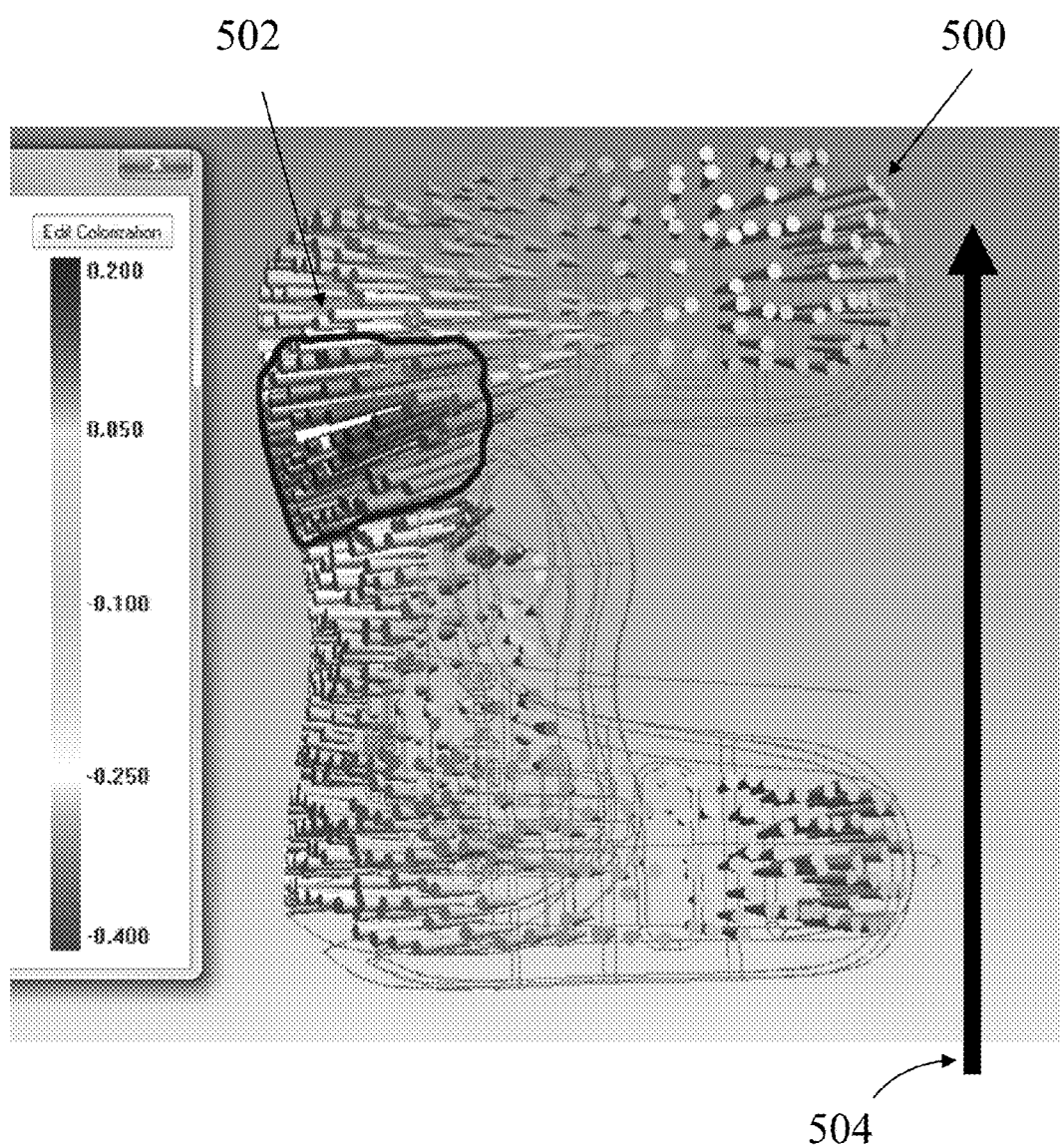
FIG. 4 depicts an exemplary finite element analysis of a femoral implant.
Figure 5:
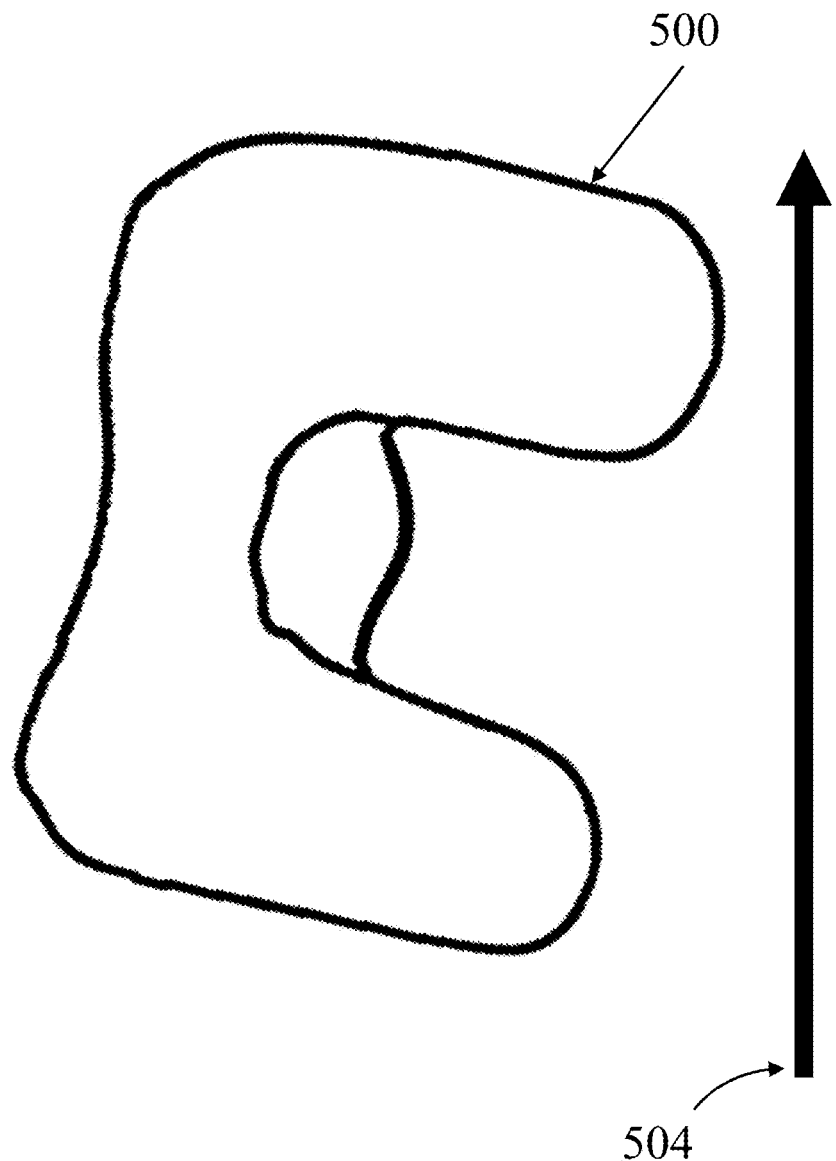
FIG. 5 depicts a corrected build orientation for a femoral implant.

FIG. 4 illustrates an example of a localized deviation in a femoral implant 500. Visually represented in FIG. 4 is a comparison of the spatial coordinates of a plurality of points on the surface of a physical implant 500 relative to the spatial coordinates of the corresponding points in the implant's design. The comparison shows that the surface of the physical implant in region 502 slightly bulges, that is it deviates by a relative magnitude of greater than 0.25, from the implant design. This can be the result of, for example, a lack of support for the build material in region 502, as it can be seen that, starting generally from the lowest point of this region relative to the build direction 504, the material forming the implant surface begins extending laterally (i.e., within the plane perpendicular to the build direction) beyond the implant portions immediately below. In some exemplary embodiments, the alignment/orientation of implant 500 may be rotated relative to the build direction 504, as depicted in FIG. 5, such that region 502 is more directly supported by portions of the implant that are lower in the build direction. Accordingly, upon manufacturing the implant in this modified alignment/orientation, the additional support may help to reduce or eliminate the local deviation in region 502.

In embodiments where the alignment/orientation of implant 500 is rotated relative to the build direction 504, the magnitude of the angle of rotation used may vary depending on additional requirements/considerations for the particular embodiment. For example, if the highest priority is elimination of the localized deviation, the magnitude of the angle of rotation may be approximately the minimum value needed to ensure that no portion of the implant surface in region 502 extends within the plane perpendicular to the build direction beyond the implant portions immediately below (referred to hereafter as a "max compensation angle"). Rotation of the implant to address a particular localized deviation may, however, result in otherwise undesired changes to the support structure requirements for other portions of the implant. Accordingly, in certain embodiments, it may be advantageous to utilize the minimum rotation angle that will still result in additional support for the region 502 and sufficiently reduce the local deviation in region 502, while not necessarily entirely eliminating the deviation. Thus, certain embodiments may include an automated or manual step of iteratively rotating implant 500 relative to build direction 504 and assessing the impact on the localized deviation of interest.

During such a process for selecting the magnitude of the angle of rotation to be used, in addition to the impact on the localized deviation of interest, the impact of the rotation on other aspects of the design and/or manufacturing plan (e.g., need for supporting structures, as discussed above, and/or effects associated with anisotropic properties of the final implant, as discussed in greater detail below) may be considered. For example, in certain embodiments, the magnitude of the angle of rotation may be arrived at by a balancing of the goals of providing sufficient support for the local deviation and minimizing the amount of additional support structure required elsewhere. Additionally or alternatively, the magnitude of the angle of orientation may be a portion or percentage of the max compensation angle that has been determined generally beneficial, such as, for example, approximately 25%, 50%, or 75% of the max rotation angle.

Where two or more implants are to be manufactured in a single run within a single build chamber, the opportunity may exist to connect or otherwise attach various surfaces (i.e., adjacent surfaces or surfaces proximate to each other) of the different implants to each other, thereby providing additional supports and/or anchoring of the implants. Such an arrangement can significantly improve the stability of the connected component(s), can provide additional heat sinks for dissipation of thermal energy during melt pool formation, and can potentially reduce the need for other support structures, or may allow for less robust structures to be utilized to support and/or anchor a given build object. In many cases, the positioning and orientation of implants can be modified to facilitate such interconnection, by placing the objects in close proximity within the build chamber and designing interconnecting features for the SLM/DMLS equipment to manufacture as part of the build process.

Figure 6:
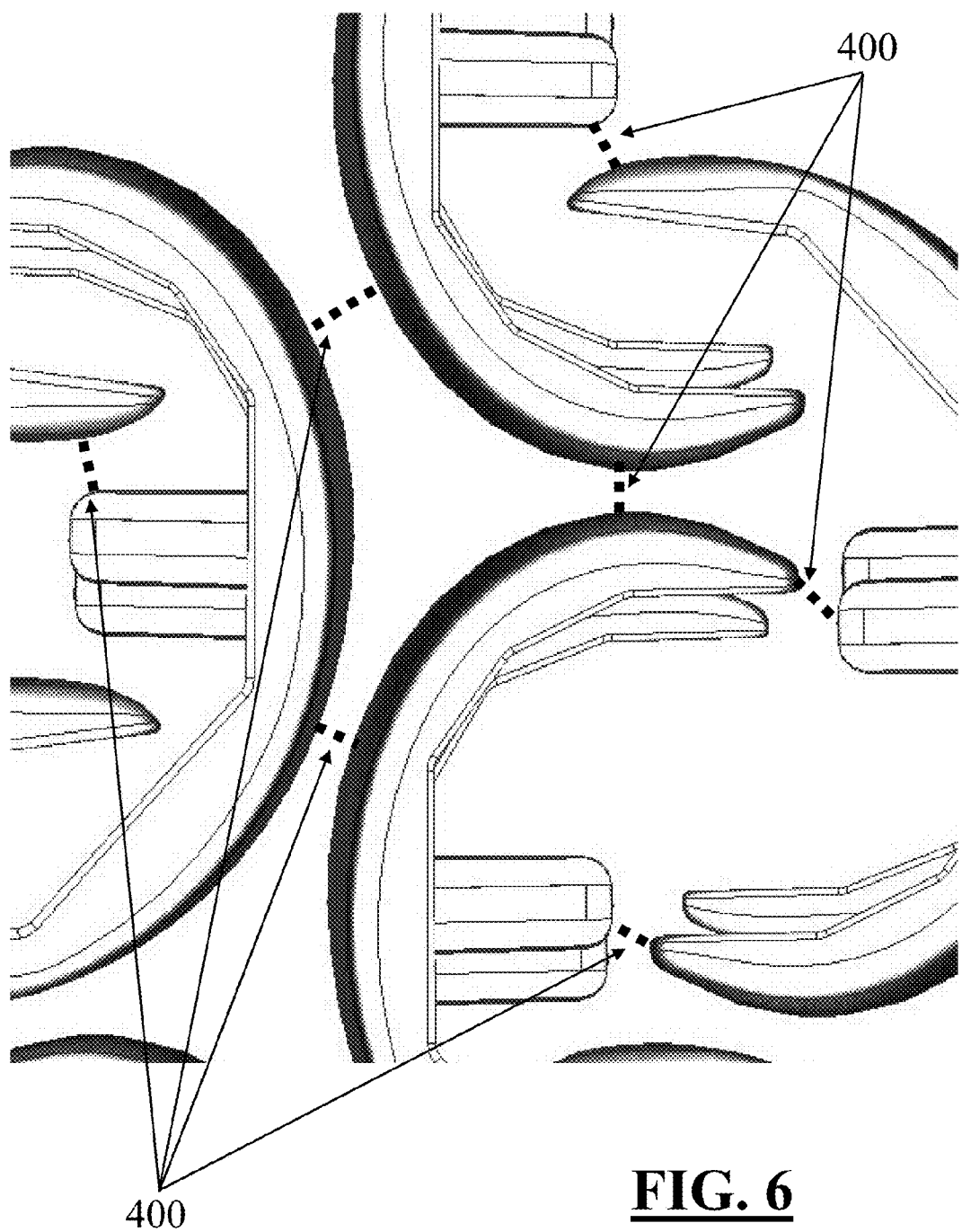
FIG. 6 depicts a partial view of the of the build plan of FIG. 11.
Figure 11:
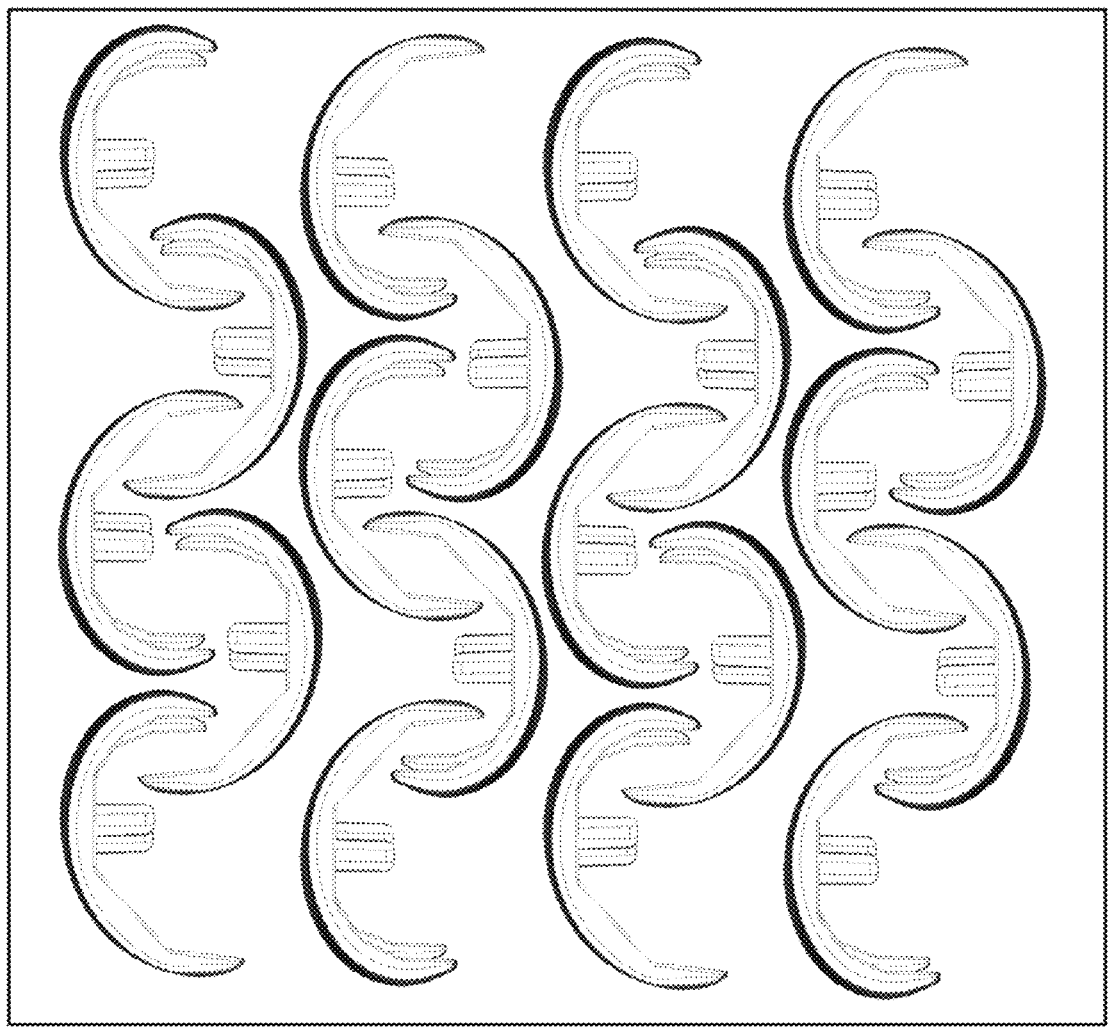
FIG. 11 depicts an exemplary interleaved object build plan for a plurality of femoral implant components.

FIG. 6 depicts a partial view of the of the build plan of FIG. 11, in which a series of interconnecting anchors 400 have been designed into the build plan. These anchors 400 can extend between adjacent surfaces of adjacent implants, and can be removed after the SLM/DMLS build has been completed. Desirably, the anchors will be relatively less robust as compared to the implant construction, so as to allow the anchors to be easily broken and/or otherwise separated.

The separation of individual build objects can also be an important consideration in the placement of inter-implant connections to desirably facilitate separation of the respective implant components from one another. In such a case, such as the connections depicted in FIG. 9, the substrate may be initially removed from the built objects, and then a cutting device such as a vertical saw blade (or similar low-profile cutting device) may be used to separate the inter-object connections in a desirable manner without damaging the individual components. Moreover, the interconnection may be designed to permit simple flexing and/or manipulation of the individual implant components to slightly work-harden and/or fracture the interconnection by simple hand manipulation, any remaining fragments of the interconnection being removed from the implant during the finishing phase.

In various embodiments, it may not be desirable for various adjacent surfaces to be connected in this manner. For example, an implant designer may not wish for interior portions of a given implant to serve as anchoring points. In such a case, the implant dataset may include information that includes or excludes various implant surfaces as attachment points, and the packing software and/or an operator can subsequently identify adjacent implant areas that allow interconnection for potential interconnection point(s).

Setting and Weighing Parameters

As described herein, various embodiments can apply modeling, for example, virtual modeling and/or mathematical modeling, to identify optimum implant component placement and orientation, as well as optimal implant features and measurements, to achieve or advance one or more parameter targets or thresholds in a packing plan. For example, a plurality of implant models can be used to identify, select, and/or design an implant packing arrangement relative to selected parameters contained in one or more datasets of the implant components and, optionally, relative to other parameters external to the datasets. In certain embodiments, an operator, physician, clinician, or other user can select one or more parameters, parameter thresholds or targets, and/or relative weightings for various parameters considered and/or included in the model.

Certain embodiments described herein include generating and/or using models, for example, virtual models of orthopedic implants that include selected parameters and/or parameter measurements, and virtually positioning and/or orienting the implant models to fit a virtual model of a SLM/DMLS build chamber with the selected parameters and/or parameter measurements. This approach can allow for iterative selection and/or design improvement and can include steps to virtually assess fit relative to the selected parameters and/or parameter measurements, such as (1) maximum implant count; (2) maximum fused-powder density; (3) optimized manufacture of critical and/or time sensitive implant components; (4) efficient use of build chamber volume; (5) efficient use of build chamber substrate surface area; (6) optimal placement of implant components to obtain desired spacing and/or provide for mutual support and/or anchoring between individual objects; and (7) optimizing implant decoupling plan for separation from underlying substrate and/or any adjacent implant components.

One or more parametric thresholds and/or weightings can be applied for the selection and/or designing process. Different parameters can have the same weighting or they can have different weightings. A parameter can include one or more thresholds for selecting one or more implants. The thresholds can include one or more minimum threshold values (e.g., with different weightings), for example, 80%, greater than 80%, 85%, greater than 85%, 90%, greater than 90%, 95%, greater than 95%, 97%, greater than 97%, 98%, greater than 98%, 99%, greater than 99%, 100%, and/or greater than 100% a target value, such as optimal or desired range of implant orientations. Alternatively or in addition, the thresholds can include one or more maximum threshold values (e.g., with different weightings), such as 105%, less than 105%, 103%, less than 103%, 102%, less than 102%, 101%, less than 101%, 100%, and/or less than 100% a target value, such as maximum amount a given parameter can be exceeded or "stretched" before the system prohibits such actions and moves on to other datasets for evaluation.

One or more parameter thresholds can be absolute, for example, by selecting and/or designing for only virtual volume(s) that meet the threshold, for example, an implant size and/or shape. An example of a selection and/or design process having multiple absolute thresholds is a process that allows for vertical rotation and/or "flipping" of an implant dataset along a given laser scan direction.

Alternatively or in addition, one or more parameter thresholds can be contingent on one or more other factors. In particular, a selection and/or designing process can successively search a database for implant datasets based on contingent thresholds. For example, an implant component dataset may meet a minimum size and/or volume threshold, but a scheduling threshold may indicate the manufacture of the implant is non-critical. If no other implant dataset meets the required threshold, or if some implant datasets meet the threshold but do not meet other parameter thresholds, then a second selection round can include implant datasets meeting a subsequently modified threshold. The process can continue to use additional, contingent thresholds until an implant dataset with the selected parameter thresholds is identified. If desired, different thresholds can be defined for different implant datasets, and identical thresholds from different datasets may be assessed differently based on other thresholds.

Any of the methods described herein can be performed, at least in part, using a computer-readable medium having instructions stored thereon, which, when executed by one or more processors, causes the one or more processors to perform one or more operations corresponding to one or more steps in the method. Any of the methods can include the steps of receiving input from a device or user and producing an output for a user, for example, a physician, clinician, technician, or other user. Executed instructions on the computer-readable medium (i.e., a software program) can be used, for example, to receive as input patient-specific information (e.g., images of a patient's implant structure) and provide as output a virtual model of the patient's implant structure. Similarly, executed instructions on a computer-readable medium can be used to receive as input patient-specific information and user-selected and/or weighted parameters and then provide as output to a user values or ranges of values for those parameters and/or for implant component features. For example, in certain embodiments, patient-specific implant information can be input into a computer software program for selecting and/or designing one or more packing plans for the SLM/DMLS manufacture of implant components, and the program can output one or more optimized plans for further assessment and/or use by the operator.

Optimization of multiple parameters may result in conflicting constraints; for example, optimizing one parameter may cause an undesired deviation to one or more other parameters. In cases where not all constraints can be achieved at the same time, parameters can be assigned a priority or weight in the software program. The priority or weighting can be automated (e.g., part of the computer program) and/or it can be selected by a user depending on the user's desired design goals, for example, manufacturing time-critical implant components and/or minimization per-implant manufacturing cost, or some combination to accommodate both parameters in overall design.

In any automated process or process step performed by the computer system, constraints pertaining to a specific build chamber, SLM/DMLS manufacturing process and/or individual implant models may be taken into account. Any one or more steps of the assessment, selection, design and/or manufacture may be partially or fully automated, for example, using a computer-run software program and/or one or more robots. For example, processing of the implant datasets, the selection and packing of datasets into a virtual build chamber and/or the manufacture of selected implant components according to one or more build plan(s) may be partially or wholly automated. For example, implant datasets, with optional user-defined parameters, may be inputted or transferred by a user and/or by electronic transfer into a software-directed computer system that can identify implant component features and/or feature measurements and perform operations to generate one or more virtual models and/or packing plans, for example, in accordance with one or more target or threshold parameters.

Assessment of the various parameters, optionally with one or more additional parameters, can be conducted using various formats. For example, the assessment of one or more parameters can be performed in series, in parallel, or in a combination of serial and parallel steps, optionally with a software-directed computer. Any one or more of the parameters and features and/or feature measurements can be the first to be selected and/or designed. Alternatively, one or more, or all, of the parameters and/or features can be assessed simultaneously.

The assessment process can be iterative in nature. For example, one or more first parameters from a first dataset can be assessed and the related implant component features within the virtual build chamber (i.e., implant placement and orientation) can tentatively or conditionally be determined. Next, one or more second parameters from a second dataset can be assessed and, optionally, one or more second implant features within the virtual build chamber measurements determined. Then, the tentative or conditional features and/or feature measurements for the first assessed parameter(s) optionally can be altered based on the assessment and optional determinations for the second assessed parameters. The assessment process can be fully automated or it can be partially automated allowing for user interaction. User interaction can be particularly useful for quality assurance purposes.

In the assessment, different weighting can be applied to any of the parameters or parameter thresholds, for example, based on the patient's age, the scheduled surgery date, various implant cost targets provided by a patient and/or insurer, the surgeon's preference or the patient's preference. Feedback mechanisms can be used to show the user or the software the effect that certain feature and/or feature changes can have on desired changes to parameters values, e.g., relative to selected parameter thresholds. For example, a feedback mechanism can be used to determine the effect that changes in various features intended to maximize build efficiency have on other parameters such as estimated build time and/or powder wastage, for example. Accordingly, implant datasets can be modeled virtually and modified reiteratively to achieve an optimum solution for a particular patient, groups of patients and/or a given build run.

Various embodiments described herein include designs and methods to mitigate, reduce and/or eliminate structural and/or processing challenges and/or concerns posed by SLM/DMLS manufacturing of implant components. In addition, various embodiments further include designs and methods that improve, maximize and/or take advantage of structural and/or processing benefits conferred by SLM/DMLS manufacturing of implant components. In addition, various additional techniques, such as laser polishing or laser rescanning in parallel and/or perpendicular scanning directions (including remelting of previously formed surfaces and/or structures), hot isostatic processing (HIP) processing of manufactured implants, annealing and/or coating (i.e., titanium nitride coating and/or titanium aluminum nitride coating) are contemplated for use with the various embodiments disclosed herein.

Post SLM/DMLS-Manufacture Processing Steps

In various embodiments, the design and manufacture of an implant component using SLM/DMLS manufacturing methods may include additional processing and/or finishing steps which are not mandated, required and/or are necessary to prepare the part for use and implantation when the part is manufactured using convention methods (i.e., casting, wrought and/or machining, etc.). For example, if the surface porosity of an implant created via SLM/DMLS manufacturing is unacceptable for a given application, it may be necessary to remove and/or fill the pores using a variety of additional manufacturing and/or finishing steps, which can include coating, filling, remelting, HIP-ping, annealing and/or machining, as well as potentially adding additional material to the implant surface to facilitate subsequent conventional material removal or modification processes (i.e., machining or working hardening of the SLM/DMLS object), or to allow for additional polishing and/or grinding to remove the undesired surface features. Various embodiments described herein include the use of such additional processes to "finish" a SLM/DMLS part, including the use of such processes on a localize portion of the implant (i.e., performed only on the articulating surfaces or other implant surfaces having undesirable features or characteristics).

In various embodiments, a wide variety of standard finishing techniques used with cast or wrought implants, such as polishing, drag finishing, machining and/or bead/grit blasting, may be used to finish SLM/DMLS parts as well, with varying results.

EXAMPLES

In one exemplary embodiment, an automated and/or semi-automated system can be employed to create an optimized packing plan resulting in an "interleaved" build configuration. FIG. 11 depicts one exemplary interleaved object build plan for a plurality of femoral implant components. While the components depicted in the figure are substantially the same shape and size, a similar interleaved configuration could be employed created to a build plan that accommodates implant components of differing shapes, sizes and/or designs.

Figure 13:
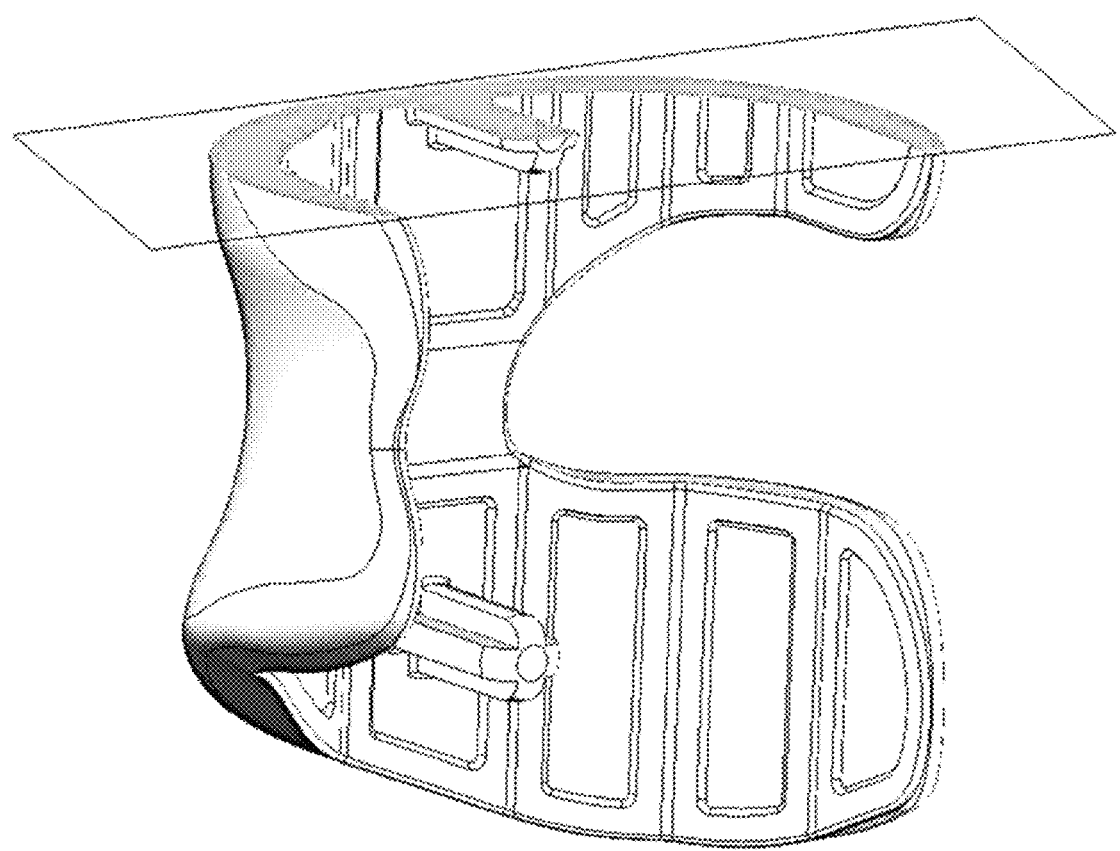
FIG. 13 depicts an implant component with an exemplary melt layer aligned essentially parallel to a plane perpendicular to the medial-lateral axis of the implant component.
Figure 14:
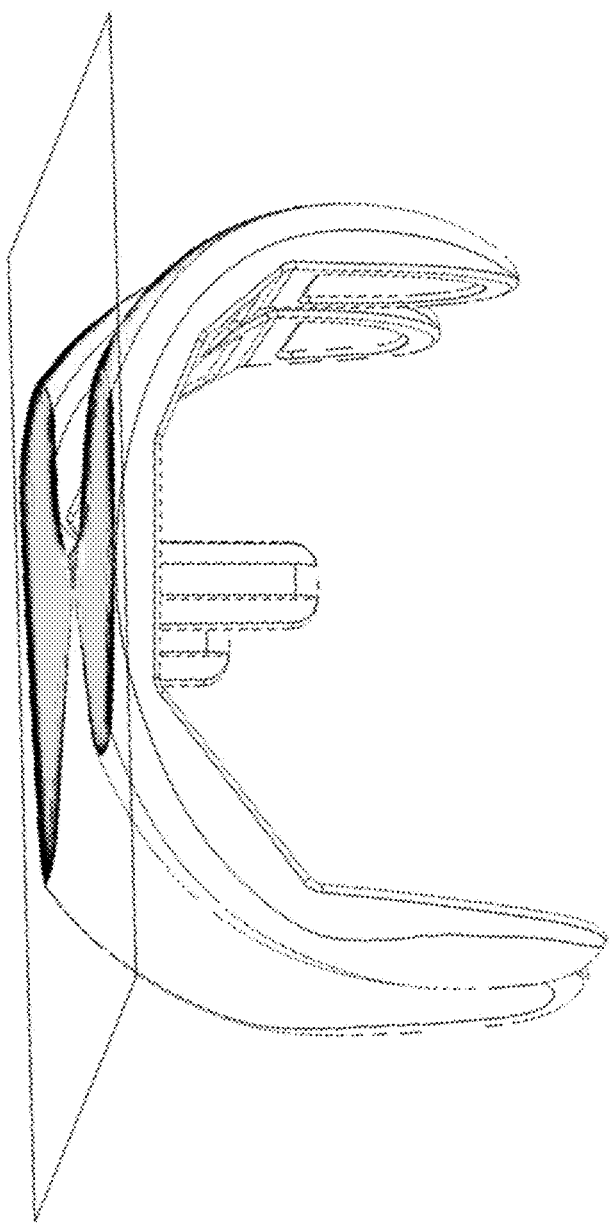
FIG. 14 depicts an implant component with an exemplary scan lines orientation aligned essentially parallel to a plane that is perpendicular to the cephalad-caudad axis of the implant component.

In FIG. 11, the outer boundary can represent the interior walls of a SLM/DMLS build chamber (or the extent of a substrate platform contained therein), which in one embodiment could be 250 mm×250 mm, a common chamber size for a commercially available SLM/DMLS machine. Utilizing this build plan, a total of twenty (20) femoral implant components can be manufactured in a single build run, with sufficient spacing between adjacent objects to prevent unwanted contact and/or adhesion between objects and/or allow desired interconnections between build objects. Moreover, this plan could accommodate an orientation limitation on the manufacture of the implant component, in which the various melt layers are aligned essentially parallel to a plane that is perpendicular to the medial-lateral axis of the implant component (see FIG. 13), and the individual scan lines could be aligned essentially parallel to a plane that is perpendicular to the cephalad-caudad axis of the implant component (see FIG. 14). This arrangement can be accomplished by orienting the implant in either an upright or "flipped" orientation, as depicted by the two opposing object orientations of FIG. 11.

In the embodiment of FIG. 11, the series of patient-specific femoral implant design files are virtually positioned in an "interleaved" fashion, with the medial/lateral sides of the implant oriented in a vertical fashion, and one side edge of each component facing approximately towards a virtual substrate surface. This alignment desirably orients the intended "build lines" of each SLM/DMLS layer along one or more directions where implant stresses are minimized or otherwise accommodated, thereby reducing the potential for implant fracture and/or material failure along one or more of the build lines. Moreover, this arrangement facilitates the creation of femoral implants having different medial-lateral widths in a single SLM/DMLS build, as some larger implants can extend "higher" into the build chamber without interfering with other, smaller implants.

Figure 12:
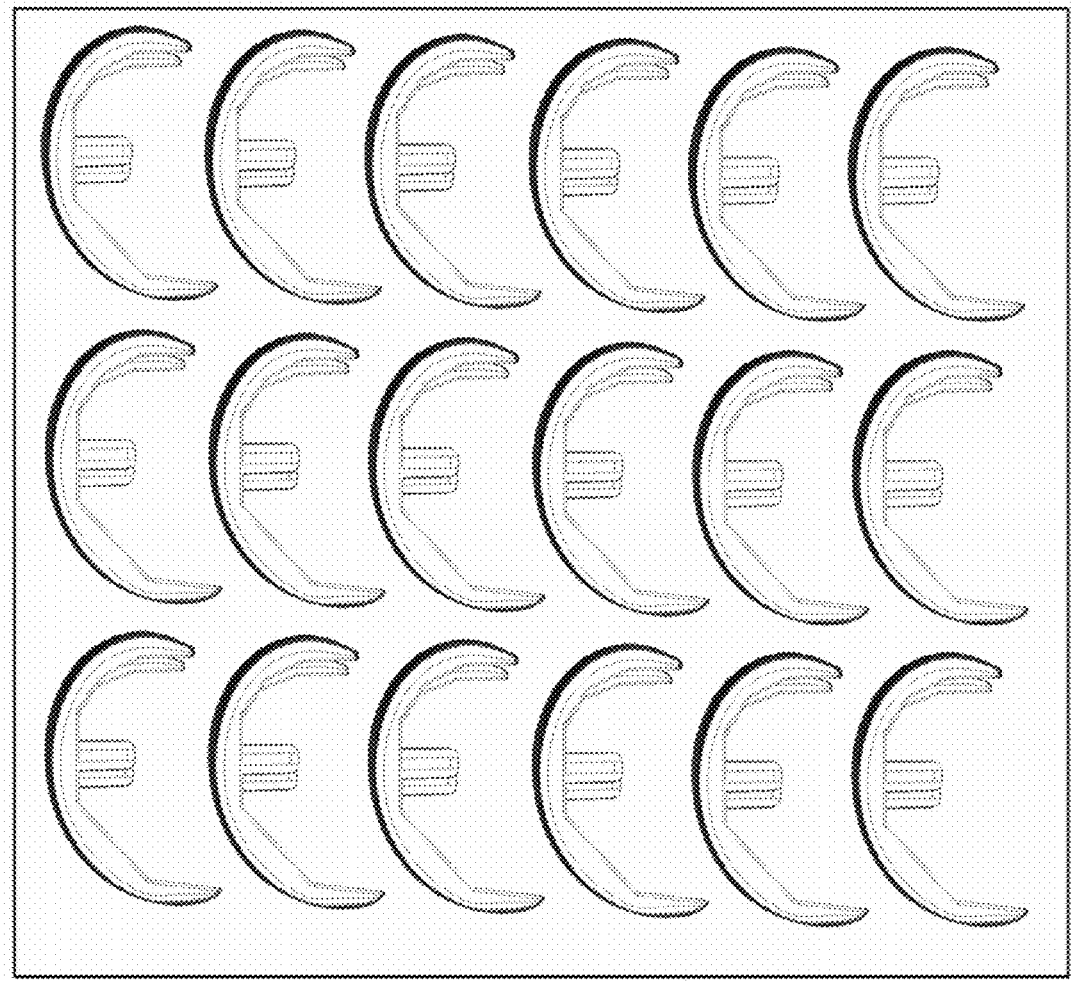
FIG. 12 depicts another "repetitive" object build plan for a plurality of femoral implant components.

In contrast, FIG. 12 depicts a packing plan utilizing a "repetitive" build configuration, which would create a total of eighteen (18) femoral implant components in a single build run for the same sized chamber, with sufficient spacing between adjacent objects to prevent unwanted contact and/or adhesion between objects. While the packing plan of FIG. 12 preserves the desired implant orientation for manufacture, and might be desirable in various circumstances, the packing plan in the manner depicted in FIG. 11 optimizes both implant build efficiencies and build orientation, resulting in an increased build output of a single SLM machine by more than 10% over the non-optimized build plan of FIG. 12.

Depending upon various boundary conditions and/or other constraints, further optimization of a packing plan can occur. For example, where the orientation of the implant components is not significantly limited or constrained to a given build direction, the geometric freedom to rotate implant datasets during application of the packing algorithm can further increase the number of build components in a single run. In addition, the ability to "stack" or otherwise allow for three-dimensional freedom within a given build chamber volume (i.e., building objects on top of one another) could potentially further increase object build efficiencies, if the chosen manufacturing method is capable of such manufacturing.

Other Implants

In a manner similar to the various embodiments described herein in connection with femoral implant components, a plurality of tibial tray components could be manufactured using additive techniques such as laser sintering, selective laser melting, direct metal laser sintering or electron beam melting or otherwise constructed out of a metal or metal alloy such as cobalt chromium. Similarly, an insert component could be manufactured through rapid prototyping or additive techniques or otherwise constructed out of a plastic polymer such as ultra high molecular weight polyethylene. Other known materials, such as ceramics including ceramic coating, may be used as well, for one or both components, or in combination with the metal, metal alloy and polymer described above. It should be appreciated by those of skill in the art that an implant may be constructed as one piece out of any of the above, or other, materials, or in multiple pieces out of a combination of materials. For example, a tray component constructed of a polymer with a two-piece insert component constructed one piece out of a metal alloy and the other piece constructed out of ceramic.

Figure 9:
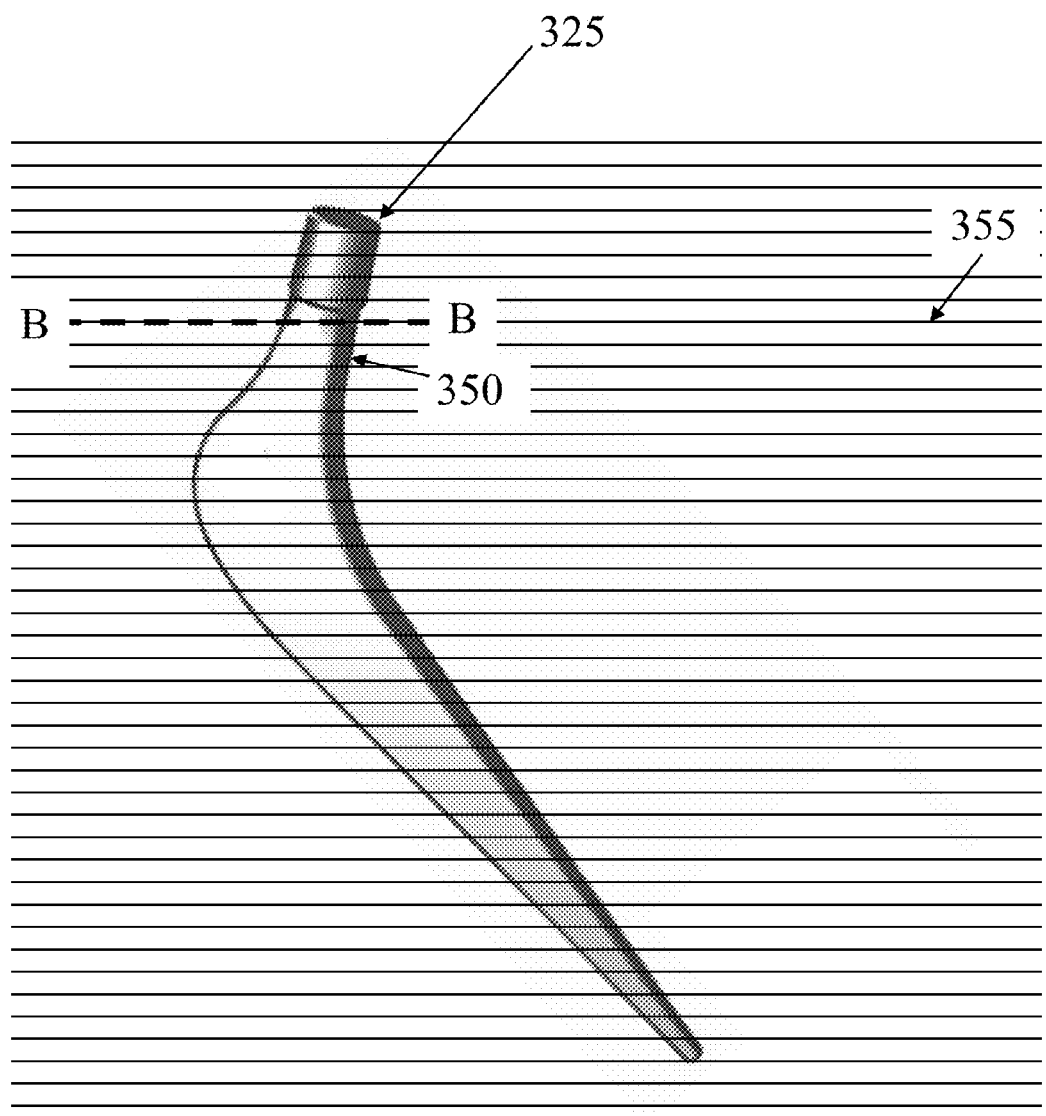
FIG. 9 depicts a simplified view of a hip stem with SLM/DMLS layers used to create the implant.
Figure 10:
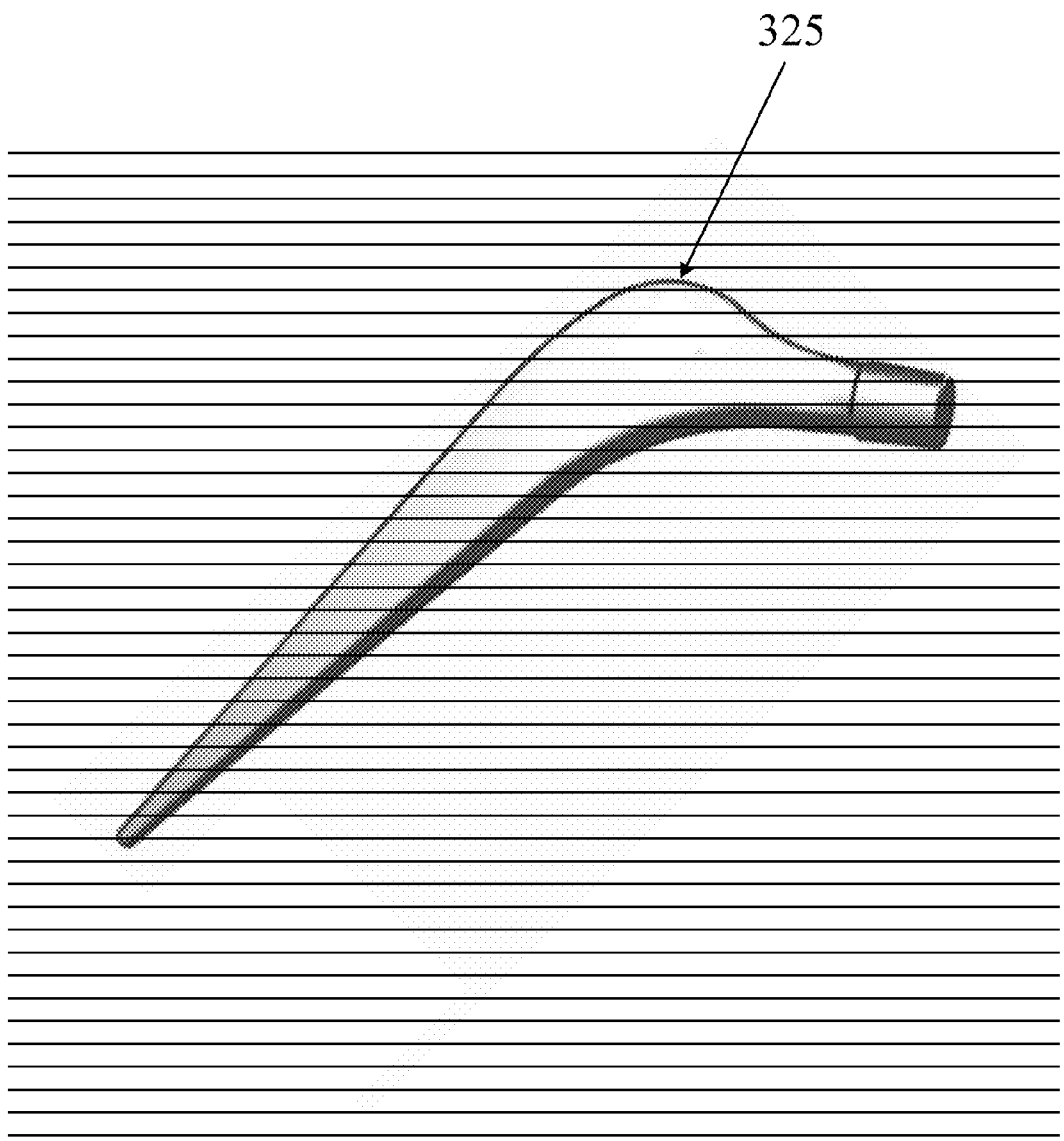
FIG. 10 depicts the hip stem of FIG. 9 with a modified manufacturing orientation.

While the various embodiments and teachings therein are described with regards to a knee joint, the various embodiments described herein can be applied to various other joints or joint surfaces in the body, e.g., a knee, hip, ankle, foot, toe, shoulder, elbow, wrist, hand, and a spine or spinal joints. For example, the material properties of a hip stem manufactured using SLM/DMLS techniques may similar be dependent upon the orientation and/or alignment of the design during manufacture. FIG. 9 depicts a hip stem 325 and a plurality of horizontal layers (shown as the parallel horizontal lines in the figure, which is a greatly simplified representation of the numerous layers used to create the implant) representing the SLM/DMLS manufacturing process. An FEA or other analysis of the implant, which optionally may include material property information particular to the type of manufacturing processes as well as the design and orientation of the implant, may identify one or more locations of high stress and/or areas of localized implant weakness. One such region that could be prone to fracture and/or failure could be a portion of the implant in the vicinity of region B-B, which includes a region where maximum implant stresses (for example, along the neck 350 of the implant) approximately meets a horizontal layer 355 created during the SLM manufacturing process. In such a case, it may be desirous to increase the local implant thickness proximate this region and/or alter the orientation of the implant during manufacture to reduce the fracture potential along this layer, if the implant cannot accommodate the required and/or estimated forces. FIG. 10 depicts the same hip stem 325, where rotation of the implant design during manufacture could potentially reduce the potential for such neck fractures due to localized material conditions and/or fracture planes.

Materials

Any material known in the art can be used for any of the implant systems and component described in the foregoing embodiments, for example including, but not limited to metal, metallic powders, metal alloys, combinations of metals, plastic, polyethylene, cross-linked polyethylene's or polymers or plastics, pyrolytic carbon, nanotubes and carbons, as well as biologic materials.

In various exemplary embodiments, the SLM raw material can comprise a CrCo powder having an average particle size of between 34 and 54 microns, although the use of larger and/or smaller particles may used with varying degrees of utility (as well as the use of differing size particles in creating a single implant component). In various embodiments, the deposed particle layer may be approximately 60 microns thick which, when melted, consolidated and cooled, can create a solid structural layer of approximately 20 microns thickness.

Any fixation techniques and combinations thereof known in the art can be used for any of the implant systems and component described in the foregoing embodiments, for example including, but not limited to cementing techniques, porous coating of at least portions of an implant component, press fit techniques of at least a portion of an implant, ingrowth techniques, etc.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

What is claimed is:

1. A method of manufacturing a plurality of orthopedic implant components, the method comprising: providing a design for a first implant component having at least one dimension that is based on patient-specific information and a design for a second implant component having at least one dimension that is based on patient specific information; creating a build plan that includes a position and orientation for at least each of the first and second implant components within a build chamber of a solid freeform fabrication machine and with respect to a platform of the build chamber; and producing the implants included in the build plan by executing a build run of the solid freeform fabrication machine based on the build plan, wherein the plurality of implant components are positioned and oriented in an interleaved build configuration according to the build plan, wherein the first and second implant components comprise femoral implant components and each has a medial-lateral width, wherein the medial-lateral width of the first implant component is different than the medial-lateral width of the second implant component.

2. The method of claim 1, wherein, according to the build plan, a medial side edge of the first implant component faces the platform and a lateral side edge of the second implant component faces the platform.

3. The method of claim 1, wherein creating the build plan comprises optimizing an alignment of each of the first and second implant components with respect to one or more components of the solid freeform manufacturing machine selected form the group of components consisting of a laser, a powder depositor and leveler, and a powder bed.

4. The method of claim 1, wherein, according to the build plan, each of the first and second implant components are aligned in the same direction with respect to a powder depositor and leveler of the solid freeform manufacturing machine.

5. The method of claim 1, further comprising providing a design for a third implant component, wherein, according to the build plan, at least a portion of the second implant is positioned in the build plan between the first implant component and the third implant component, the third implant component is oriented in the same direction as the first implant component within the build chamber, and the second implant component is oriented in a different direction than the first implant component within the build chamber.

6. The method of claim 1, wherein, according to the build plan, melt layers of the solid freeform fabrication machine are aligned essentially parallel to a plane that is perpendicular to a cephalad-caudad axis of the first and second implant components.

7. The method of claim 1, wherein the medial and lateral sides of the femoral implant components are oriented in a vertical fashion in the build plan, with one side edge of each component facing approximately towards a virtual substrate surface.

8. A method of manufacturing a plurality of orthopedic implant components, the method comprising: providing a design for a first implant component having at least one dimension that is based on patient-specific information and a design for a second implant component having at least one dimension that is based on patient specific information; creating a build plan that includes a position and orientation for at least each of the first and second implant components within a build chamber of a solid freeform fabrication machine and with respect to a platform of the build chamber; and producing the implants included in the build plan by executing a build run of the solid freeform fabrication machine based on the build plan, wherein the plurality of implant components are positioned and oriented in an interleaved build configuration according to the build plan, wherein the first implant component comprises a femoral implant component and the second implant component comprises a tibial implant component.

9. The method of claim 8, wherein, according to the build plan, a medial side edge of the first implant component faces the platform and a lateral side edge of the second implant component faces the platform.

10. The method of claim 8, wherein creating the build plan comprises optimizing an alignment of each of the first and second implant components with respect to one or more components of the solid freeform manufacturing machine selected form the group of components consisting of a laser, a powder depositor and leveler, and a powder bed.

11. The method of claim 8, wherein, according to the build plan, each of the first and second implant components are aligned in the same direction with respect to a powder depositor and leveler of the solid freeform manufacturing machine.

12. The method of claim 8, further comprising providing a design for a third implant component, wherein, according to the build plan, at least a portion of the second implant is positioned in the build plan between the first implant component and the third implant component, the third implant component is oriented in the same direction as the first implant component within the build chamber, and the second implant component is oriented in a different direction than the first implant component within the build chamber.

13. The method of claim 8, wherein, according to the build plan, melt layers of the solid freeform fabrication machine are aligned essentially parallel to a plane that is perpendicular to a cephalad-caudad axis of the first and second implant components.

* * * * *